United States Patent
Nagai et al.

(10) Patent No.: US 10,881,381 B2
(45) Date of Patent: Jan. 5, 2021

(54) ULTRASONIC DIAGNOSTIC SYSTEM

(71) Applicant: General Electric Company, Schenectady, NY (US)

(72) Inventors: Saika Nagai, Tokyo (JP); Teck Chuan Beh, Tokyo (JP); Naohisa Kamiyama, Tokyo (JP)

(73) Assignee: General Electric Company, Schenectady, NY (US)

( * ) Notice: Subject to any disclaimer, the term of this patent is extended or adjusted under 35 U.S.C. 154(b) by 471 days.

(21) Appl. No.: 15/851,072

(22) Filed: Dec. 21, 2017

(65) Prior Publication Data

US 2018/0177492 A1 Jun. 28, 2018

(30) Foreign Application Priority Data

Dec. 27, 2016 (JP) ................. 2016-252412

(51) Int. Cl.
 *A61B 8/08* (2006.01)
 *A61B 8/00* (2006.01)
(52) U.S. Cl.
 CPC .......... *A61B 8/5207* (2013.01); *A61B 8/4477* (2013.01); *A61B 8/485* (2013.01); *A61B 8/54* (2013.01); *A61B 8/4488* (2013.01); *A61B 8/4494* (2013.01); *A61B 8/461* (2013.01); *A61B 8/5246* (2013.01); *A61B 8/5292* (2013.01); *A61B 8/565* (2013.01)
(58) Field of Classification Search
 CPC ... A61B 8/4477; A61B 8/4488; A61B 8/4494; A61B 8/461; A61B 8/485; A61B 8/5207; A61B 8/5246; A61B 8/5292; A61B 8/54; A61B 8/565
 See application file for complete search history.

(56) References Cited

U.S. PATENT DOCUMENTS

2010/0010346 A1* 1/2010 Greenleaf .............. A61B 5/442
600/438

FOREIGN PATENT DOCUMENTS

| JP | 2004089362 A | | 3/2004 |
|----|--------------|---|--------|
| JP | 4451309 | | 11/2005 |
| JP | 2015058010 A | | 3/2015 |
| JP | 2016022297 A | * | 2/2016 |
| WO | 2011001776 | | 1/2011 |

OTHER PUBLICATIONS

Japanese Application No. 2016-252412 filed Dec. 27, 2016—Notice of Preliminary Rejection is dated Sep. 15, 2020; 7 pages.

* cited by examiner

Primary Examiner — Michael T Rozanski

(57) ABSTRACT

An ultrasonic diagnostic system comprises: a first transceiver for performing transmission/reception of first ultrasound for detecting shear waves generated in a subject by mechanical vibration; a second transceiver for performing transmission/reception of second ultrasound to/from the subject; a computing section for calculating a value of a parameter affecting a frequency of the first ultrasound to be transmitted from the first transceiver based on echo signals obtained by transmission/reception of the second ultrasound; an identifying section for identifying one first transceiver from among a plurality of kinds of first transceivers each having a different frequency of said first ultrasound based on the value of said parameter; and a display device for displaying the first transceiver identified by the identifying section.

16 Claims, 23 Drawing Sheets

ULTRASONIC DIAGNOSTIC SYSTEM

CROSS-REFERENCE TO RELATED APPLICATION

The present application claim priority from Japanese Patent Application No. JP 2016-252412 filed in the Japanese Patent Office on Dec. 27, 2016, the entire disclosure of which is hereby incorporated by reference.

FIELD OF THE INVENTION

This disclosure relates to an ultrasonic diagnostic system for detecting shear waves generated in a subject by applying mechanical vibration to the subject.

BACKGROUND OF THE INVENTION

In liver diagnosis, for example, there is a technique of quantifying hardness of the liver by applying mechanical vibration to a body surface of a subject, and detecting, by ultrasound, shear waves generated in the subject by the mechanical vibration.

BRIEF DESCRIPTION OF THE INVENTION

The frequency of the ultrasound for detecting the shear waves described above has the most suitable setting. For example, for subjects having thick subcutaneous fat, it is necessary to use a probe with relatively low frequency for reducing signal attenuation. On the other hand, for subjects having thin subcutaneous fat or pediatric subjects, ultrasound may overpenetrate and signals reflected at the diaphragm behind the liver in unexpected directions may be received, so that it is necessary to use a probe with relatively high frequency. Thus, selection of a suitable frequency is required for acquiring accurate diagnostic information. Accordingly, it is desired to provide an ultrasonic diagnostic system with which a suitable frequency can be easily selected.

The invention, in one aspect, made for solving the aforementioned problem is an ultrasonic diagnostic system comprising: a vibrator for applying mechanical vibration to a subject; a first transceiver for performing transmission/reception of first ultrasound for detecting shear waves generated in said subject by said mechanical vibration applied by said vibrator; a second transceiver for performing transmission/reception of second ultrasound different from said first ultrasound to/from said subject; a computing section for calculating a value of a parameter affecting a frequency of the first ultrasound to be transmitted from said first transceiver based on echo signals obtained by transmission/reception of said second ultrasound; an identifying section for identifying one first transceiver from among a plurality of kinds of first transceivers each having a different frequency of said first ultrasound or identifying a frequency of the first ultrasound to be transmitted/received at said first transceiver based on the value of said parameter; and a notifying section for notifying an operator of said first transceiver or said frequency identified by said identifying section.

The invention, in another aspect, is an ultrasonic diagnostic system comprising: a vibrator for applying mechanical vibration to a subject; a transceiver for performing transmission/reception of first ultrasound for detecting shear waves generated in said subject by said mechanical vibration applied by said vibrator and transmission/reception of second ultrasound different from said first ultrasound to/from said subject; a computing section for calculating a value of a parameter affecting a frequency of the first ultrasound to be transmitted from said transceiver based on echo signals obtained by transmission/reception of said second ultrasound; an identifying section for identifying a frequency of the first ultrasound to be transmitted/received at the transceiver based on the value of said parameter; and a notifying section for notifying an operator of the frequency identified by said identifying section.

The invention, in another aspect, is an ultrasonic diagnostic system comprising: a vibrator for applying mechanical vibration to a subject; a first transceiver for performing transmission/reception of first ultrasound for detecting shear waves generated in said subject by said mechanical vibration applied by said vibrator; a second transceiver for performing transmission/reception of second ultrasound different from said first ultrasound to/from said subject; a computing section for calculating a value of a parameter affecting a frequency of the first ultrasound to be transmitted from said first transceiver based on echo signals obtained by transmission/reception of said second ultrasound; an identifying section for identifying one first transceiver from among a plurality of kinds of first transceivers each having a different frequency of said first ultrasound or identifying a frequency of the first ultrasound to be transmitted/received at said first transceiver based on the value of said parameter; and a control section for performing transmission/reception of said first ultrasound with said first transceiver identified by said identifying section or with said frequency identified by said identifying section.

The invention, in another aspect, is an ultrasonic diagnostic system comprising: a vibrator for applying mechanical vibration to a subject; a transceiver for performing transmission/reception of first ultrasound for detecting shear waves generated in said subject by said mechanical vibration applied by said vibrator and transmission/reception of second ultrasound different from said first ultrasound to/from said subject; a computing section for calculating a value of a parameter affecting a frequency of the first ultrasound to be transmitted from said transceiver based on echo signals obtained by transmission/reception of said second ultrasound; an identifying section for identifying a frequency of the first ultrasound to be transmitted/received at the transceiver based on the value of said parameter; and a control section for performing transmission/reception of said first ultrasound with said frequency identified by said identifying section.

In the invention in the aspects described above, the frequency of the first ultrasound to be transmitted from said first transceiver or said transceiver is a frequency suitable for elasticity measurement on biological tissue in said subject.

According to the invention in the one aspect described above, a value of a parameter affecting a frequency of the first ultrasound to be transmitted from said first transceiver is calculated based on echo signals obtained by transmission/reception of said second ultrasound, and a first transceiver identified from among a plurality of kinds of first transceivers or a frequency of the first ultrasound is notified based on the value of the parameter, whereby an operator can find out a first transceiver for performing transmission/reception of first ultrasound with suitable frequency or the suitable frequency. A suitable frequency is thus easily selected.

According to the invention in the other aspect described above, a value of a parameter affecting a frequency of the first ultrasound to be transmitted from said first transceiver is calculated based on echo signals obtained by transmission/reception of said second ultrasound, and the frequency of said first ultrasound is notified based on the value of the parameter, whereby an operator can find out a suitable frequency. A suitable frequency is thus easily selected.

According to the invention in the other aspect described above, a value of a parameter affecting a frequency of the first ultrasound to be transmitted from said first transceiver is calculated based on echo signals obtained by transmission/reception of said second ultrasound, and transmission/reception of the first ultrasound is performed with a first transceiver identified by said identifying section or with a frequency identified by said identifying section based on the value of the parameter. A suitable frequency may thus be selected to automatically transmit/receive ultrasound of the frequency.

According to the invention in the other aspect described above, a value of a parameter affecting a frequency of the first ultrasound to be transmitted from said transceiver is calculated based on echo signals obtained by transmission/reception of said second ultrasound, and transmission/reception of the first ultrasound is performed with a frequency identified by said identifying section based on the value of the parameter. A suitable frequency may thus be selected to automatically transmit/receive ultrasound of the frequency.

DETAILED DESCRIPTION OF THE INVENTION

Figure 1:
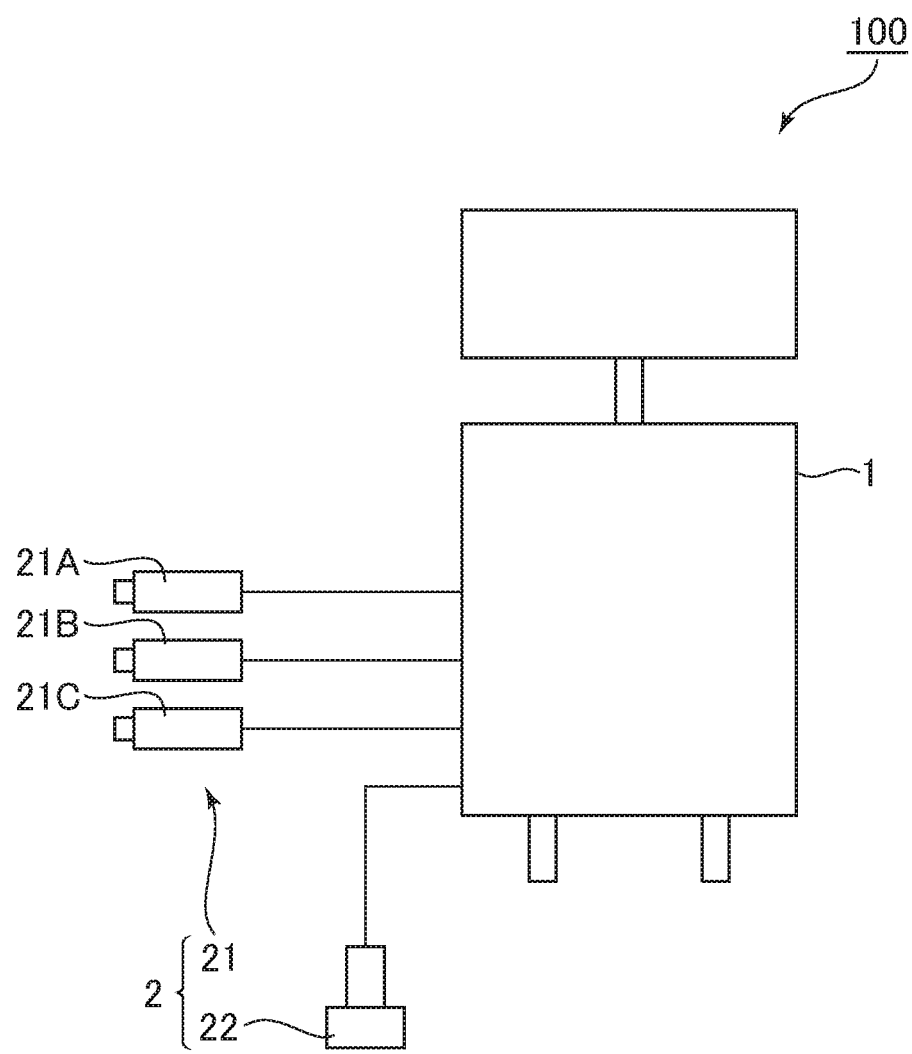
FIG. 1 is a diagram showing an outline of an exemplary ultrasonic diagnostic apparatus constituting an ultrasonic diagnostic system in a first embodiment of the present invention.

Now a first embodiment will be described first. An ultrasonic diagnostic system 100 in the first embodiment shown in FIG. 1 is comprised of an ultrasonic diagnostic apparatus 1. The ultrasonic diagnostic apparatus 1 is connected with a plurality of ultrasonic probes 2. The plurality of ultrasonic probes 2 have first ultrasonic probes 21 and a second ultrasonic probe 22. For the first ultrasonic probes 21, three first ultrasonic probes 21A, 21B, 21C are connected to the ultrasonic diagnostic apparatus 1 in the present embodiment.

Figure 2:
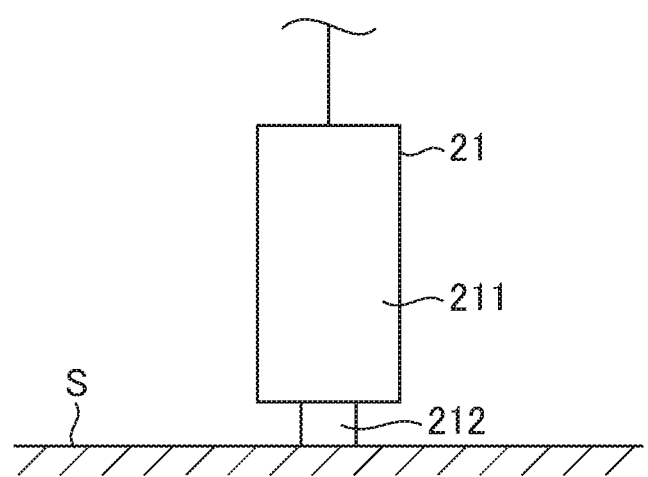
FIG. 2 is a diagram showing a first ultrasonic probe put against a body surface of a subject.

As shown in FIG. 2, a first ultrasonic probe 21 has a main body portion 211, and a vibrator 212 provided at the tip of the main body portion 211 and formed from a cylindrical protrusion. The vibrator 212 is put against a surface S of a subject, and applies mechanical vibration to the surface S. The vibrator 212 is configured to axially reciprocate with respect to the main body portion 211. It is by the axially moving vibrator 212 that mechanical vibration is applied to the subject. The vibrator 212 is an exemplary embodiment of the vibrator in the present invention.

The vibrator 212 is provided therein with at least one ultrasonic transducer, although not particularly shown. It is by the ultrasonic vibrator that first ultrasound is transmitted to an object to be measured and echo signals therefrom are received. Based on the echo signals, shear waves generated within biological tissue in the subject by the mechanical vibration by the vibrator 212 are detected, which will be discussed later. The first ultrasonic probe 21 is an exemplary embodiment of the first transceiver in the present invention.

The frequency of the first ultrasound to be transmitted/received in each of the first ultrasonic probes 21A, 21B, 21C is different from probe to probe. Moreover, the diameter of the vibrator 212 in each of the first ultrasonic probes 21A, 21B, 21C may be different from probe to probe. The diameter of the vibrator 212 may be larger for a lower frequency of the first ultrasound in the first ultrasonic probe 21.

The second ultrasonic probe 22 performs transmission/reception of second ultrasound different from the first ultrasound to/from the subject. In the ultrasonic probe 2, a plurality of ultrasonic transducers are arranged in an azimuthal direction, although not particularly shown. The second ultrasonic probe 22 is an exemplary embodiment of the second transceiver in the present invention. For example, it is by the second ultrasonic probe 22 that ultrasound for producing a B-mode image is transmitted as the second ultrasound, and echo signals therefrom are received.

Figure 3:
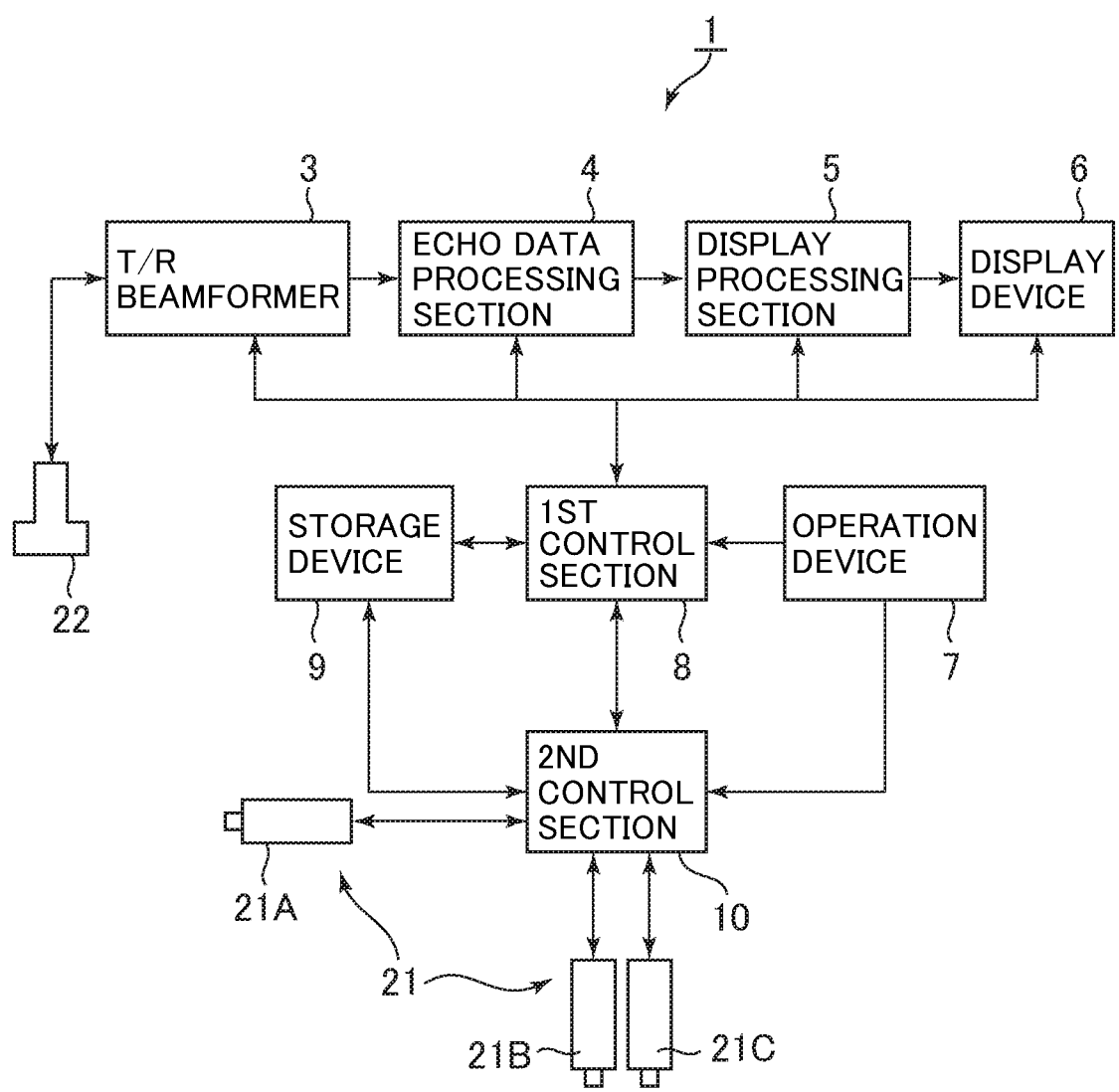
FIG. 3 is a block diagram showing a general configuration of the ultrasonic diagnostic apparatus shown in FIG. 1.

A block configuration of the ultrasonic diagnostic apparatus 1 will be described with reference to FIG. 3. In addition to the aforementioned first ultrasonic probes 21 and second ultrasonic probe 22, the ultrasonic diagnostic apparatus 1 comprises a transmission/reception (T/R) beamformer 3, an echo data processing section 4, a display processing section 5, a display device 6, an operation device 7, a first control section 8, a storage device 9, and a second control section 10. The ultrasonic diagnostic apparatus 1 is configured as a computer.

The T/R beamformer 3 drives the second ultrasonic probe 22 based on a control signal from the control section 8 to transmit second ultrasound having specific transmit parameters. The T/R beamformer 3 also performs signal processing, such as phased addition processing, on echo signals from the second ultrasound.

The echo data processing section 4 performs processing for producing an ultrasonic image on echo data output from the T/R beamformer 3. For example, the echo data processing section 4 performs B-mode processing, such as logarithmic compression processing and envelope detection processing, to create B-mode data.

Figure 4:
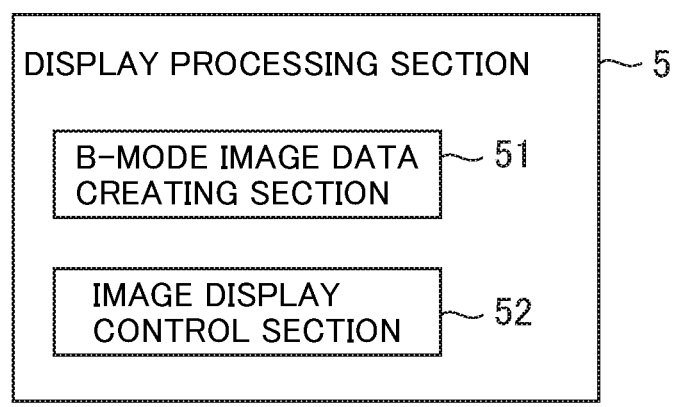
FIG. 4 is a block diagram showing a configuration of a display processing section.

The display processing section 5 has a B-mode image data creating section 51 and an image display control section 52, as shown in FIG. 4. The B-mode image data creating section 51 scan-converts the B-mode data by a scan converter to create B-mode image data. The B-mode image data creating section 51 is an exemplary embodiment of the creating section in the present invention. The B-mode image data is an example of the data for an ultrasonic image in the present invention.

The image display control section 52 displays a B-mode image on the display device 6 based on the B-mode image data. The image display control section 52 also displays text, numbers, etc. on the display device 6.

The display device 6 is an LCD (Liquid Crystal Display), an organic EL (Electro-Luminescence) display, or the like. The display device 6 is an exemplary embodiment of the notifying section in the present invention.

The operation device 7 is a device for accepting an input of a command and information from the user, although not particularly shown. The operation device 7 is configured to include buttons, a keyboard, etc. for accepting an input of a command and information from the operator, and to further include a pointing device, such as a trackball, and the like.

The first control section 8 is a processor such as a CPU (Central Processing Unit). The processor is constructed from circuitry, or the like. The first control section 8 loads thereon programs stored in the storage device 9 to control several sections in the ultrasonic diagnostic apparatus 1. For example, the first control section 8 loads thereon programs stored in the storage device 9, and executes functions of the T/R beamformer 3, echo data processing section 4, and display processing section 5 by the loaded programs.

The first control section 8 may execute all of the functions of the T/R beamformer 3, all of the functions of the echo data processing section 4, and all of the functions of the display processing section 5 by the programs, or execute only part of the functions by the programs. In the case that the first control section 8 executes only part of the functions, the remaining functions may be executed by hardware, such as circuitry.

It should be noted that the functions of the T/R beamformer 3, echo data processing section 4, and display processing section 5 may be implemented by hardware, such as circuitry.

The storage device is an HDD (Hard Disk Drive), semiconductor memory, such as RAM (Random Access Memory) and ROM (Read Only Memory), and the like. The storage device 9 includes cine memory.

The ultrasonic diagnostic apparatus 1 may have all of the HDD, RAM and ROM as the storage device 9. The storage device 9 may also be a portable storage medium, such as a CD (Compact Disk) or a DVD (Digital Versatile Disk).

The programs executed by the first control section 8 are stored in a non-transitory storage medium, such as the HDD or ROM constituting the storage device 9. The programs may also be stored in a non-transitory storage medium having portability, such as the CD or DVD, constituting the storage device 9.

Figure 5:
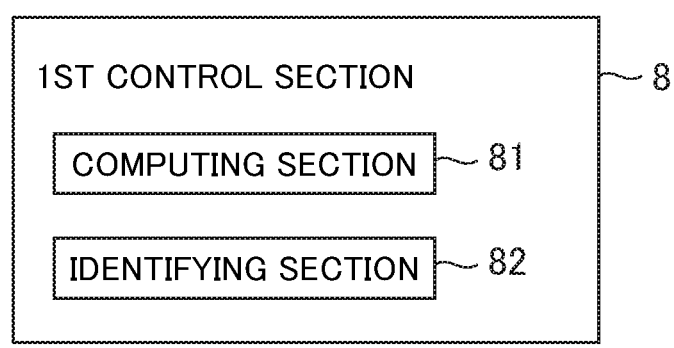
FIG. 5 is a block diagram showing exemplary functions executed by a first control section in the ultrasonic diagnostic apparatus shown in FIG. 1.

The first control section 8 executes functions of a computing section 81 and an identifying section 82 shown in FIG. 5. The computing section 81 calculates a value of a parameter affecting the most suitable frequency of the first ultrasound to be transmitted from the first ultrasonic probe 21 based on echo signals obtained by transmission/reception of the second ultrasound. Details thereof will be discussed later. The computing section 81 is an exemplary embodiment of the computing section in the present invention.

The identifying section 82 identifies one first ultrasonic probe 21 from among the first ultrasonic probes 21A, 21B, 21C or identifies one frequency of the first ultrasound from among a plurality of frequencies of the first ultrasound corresponding to the first ultrasonic probes 21A, 21B, 21C based on the value of the parameter calculated by the computing section 81. Details thereof will be discussed later. The identifying section 82 is an exemplary embodiment of the identifying section in the present invention.

Figure 6:
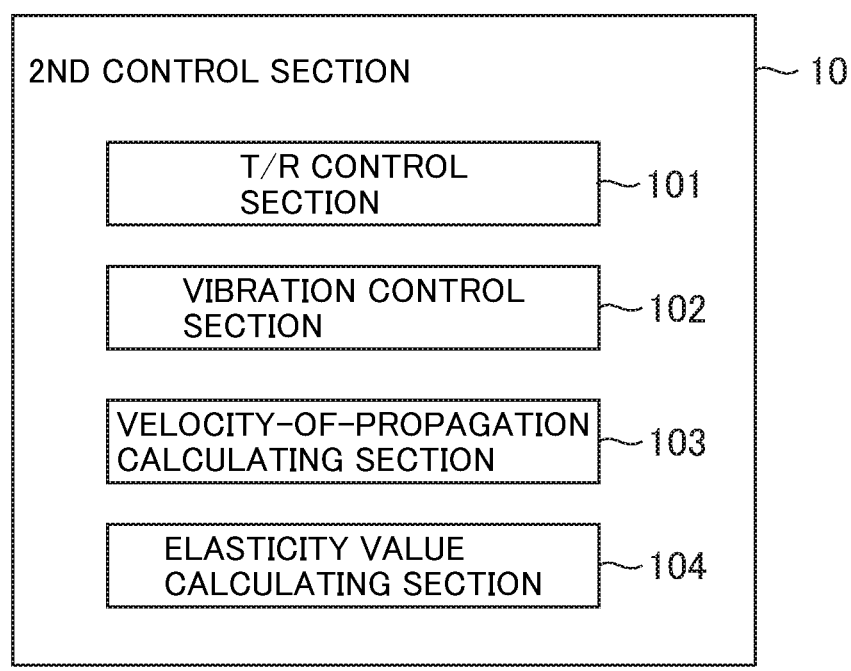
FIG. 6 is a block diagram showing exemplary functions executed by a second control section in the ultrasonic diagnostic apparatus shown in FIG. 1.

The second control section 10 is a processor such as a CPU (Central Processing Unit). The control section 8 loads thereon programs stored in the storage device 9 to perform several kinds of control. For example, the second control section 10 executes functions of a transmission/reception (T/R) control section 101, a vibration control section 102, a velocity-of-propagation calculating section 103, and an elasticity-value calculating section 104 shown in FIG. 6.

The T/R control section 101 controls transmission/reception of the first ultrasound by the first ultrasonic probe 21. The vibration control section 102 controls the operation of the vibrator 212.

The velocity-of-propagation calculating section 103 calculates a velocity V (m/sec) of propagation of the shear waves generated by mechanical vibration by the vibrator 212 based on echo signals from the first ultrasound received at the first ultrasonic probe 21. The velocity-of-propagation calculating section 42 is an exemplary embodiment of the velocity-of-propagation calculating section in the present invention.

The elasticity-value calculating section 104 calculates an elasticity value E (kPa) based on the velocity V of propagation according to (EQ. 1) below:

$$E = 3\rho V^2 \quad \text{(EQ. 1)}$$

In (EQ. 1), $\rho$ denotes the density of the object T to be measured. The elasticity value E is a modulus of elasticity.

Note that it is not always necessary to calculate the elasticity value E.

Next, an operation of the ultrasonic diagnostic apparatus 1 in the present embodiment will be described with reference to a flow chart in FIG. 7.

First, at Step S1, the second ultrasonic probe 22 performs transmission/reception of second ultrasound to/from a subject. Next, at Step S2, the B-mode image data creating section S1 creates B-mode image data for the subject based on echo signals from the second ultrasound.

Next, at Step S3, the computing section 81 calculates a value of the parameter described above based on the B-mode image data. In the present embodiment, the value of the parameter is the value of the subcutaneous fat thickness for the subject. The computing section 81 locates subcutaneous fat in the B-mode image according to image processing known in the art based on information corresponding to brightness in the B-mode image data, and calculates a value of the subcutaneous fat thickness.

The value of the subcutaneous fat thickness may be a statistical value for a plurality of positions in a horizontal direction of the B-mode image. The statistical value is a mean value, a median value, or the like, for example. By using two-dimensional information like the B-mode image data in calculating a value of the subcutaneous fat thickness, a statistical value as described above may be calculated. This gives a more reliable value of the subcutaneous fat thickness.

Next, at Step S4, the identifying section 82 identifies one first ultrasonic probe 21 from among the first ultrasonic probes 21A, 21B, 21C based on the value of the subcutaneous fat thickness obtained at Step S3. The identifying section 82 identifies a first ultrasonic probe 21 that transmits first ultrasound of lower frequency for a greater value of the subcutaneous fat thickness, while it identifies a first ultrasonic probe 21 that transmits first ultrasound of higher frequency for a smaller value of the subcutaneous fat thickness. In general, ultrasound transmitted/received at an ultrasonic probe is ultrasound in a certain frequency band. The frequency for a first ultrasonic probe 21 identified by the identifying section 82 described above is a nominal frequency (or what is generally called central frequency) for the ultrasonic probe of frequencies contained in the frequency band of ultrasound.

A table defining the relationship between a value of the subcutaneous fat thickness and each of the first ultrasonic probes 21A, 21B, 21C corresponding to the value may be stored in the storage device 9, and the identifying section 82 may identify a frequency of the first ultrasound referring to the table.

Next, at Step S5, the image display control section 52 displays characters or a geometric shape indicating the first ultrasonic probe 21 identified at Step S4 on the display device 6.

Upon display of the first ultrasonic probe 21 at Step S5, the operator uses the displayed first ultrasonic probe 21 to perform elasticity measurement at Step S6. Specifically, the operator performs an input at the operation device 7 for selecting the displayed first ultrasonic probe 21. The operator also puts the vibrator 212 of the first ultrasonic probe 21 against the body surface of the subject. Under these conditions, the vibrator 212 applies mechanical vibration to biological tissue to generate shear waves, and the first ultrasonic probe 21 transmits/receives first ultrasound for detecting the shear waves. The velocity-of-propagation calculating section 103 then calculates a velocity of propagation of the shear waves based on echo signals from the first ultrasound received at the first ultrasonic probe 21. The calculated velocity of propagation is displayed on the display device 6 by the image display control section 52. In place of or along with the velocity of propagation, an elasticity value calculated based on the velocity of propagation may be displayed on the display device 6.

According to the present embodiment described above, a first ultrasonic probe 21 that transmits first ultrasound of most suitable frequency is displayed, and therefore, the operator can easily find out which of the first ultrasonic probes 21A, 21B, 21C to use for performing elasticity measurement.

In calculation of a value of the subcutaneous fat thickness for identifying a most suitable first ultrasonic probe 21, a more reliable value of the subcutaneous fat thickness may be obtained by using B-mode image data, which is two-dimensional information.

Next, variations of the first embodiment will be described. Now a first variation will be described first. FIG. 8 is a flow chart showing an operation of the ultrasonic diagnostic apparatus in the first variation. Steps S11 to S13, and S16 shown in FIG. 8 are identical to Steps S1 to S3, and S6 shown in FIG. 7, description of which will be omitted. At Step S14, the identifying section 82 identifies a frequency of the first ultrasound based on the value of the subcutaneous fat thickness obtained at Step S13. The identifying section 82 identifies one frequency from among a frequency F1 of the first ultrasound to be transmitted from the first ultrasonic probe 21A, a frequency F2 of the first ultrasound to be transmitted from the first ultrasonic probe 21B, and a frequency F3 of the first ultrasound to be transmitted from the first ultrasonic probe 21C. The identifying section 82 identifies a lower frequency for the frequency of the first ultrasound for a greater value of the subcutaneous fat thickness, while it identifies a higher frequency for the frequency of the first ultrasound for a smaller value of the subcutaneous fat thickness. A table defining the relationship between a value of the subcutaneous fat thickness and a value of the frequency corresponding to the value may be stored in the storage device 9, and the identifying section 82 may identify a frequency of the first ultrasound referring to the table.

Next, at Step S15, the image display control section 52 displays the frequency identified at Step S14 on the display device 6. At Step S16, the operator performs an input at the operation device 7 for selecting a first ultrasonic probe 21 for transmitting first ultrasound of the frequency displayed at Step S15. Then, elasticity measurement is performed in a way similar to Step S5 described earlier. By the frequency of the first ultrasound being displayed, the operator can easily find out which of the first ultrasonic probes 21A, 21B, 21C to use for performing elasticity measurement.

Figure 8:
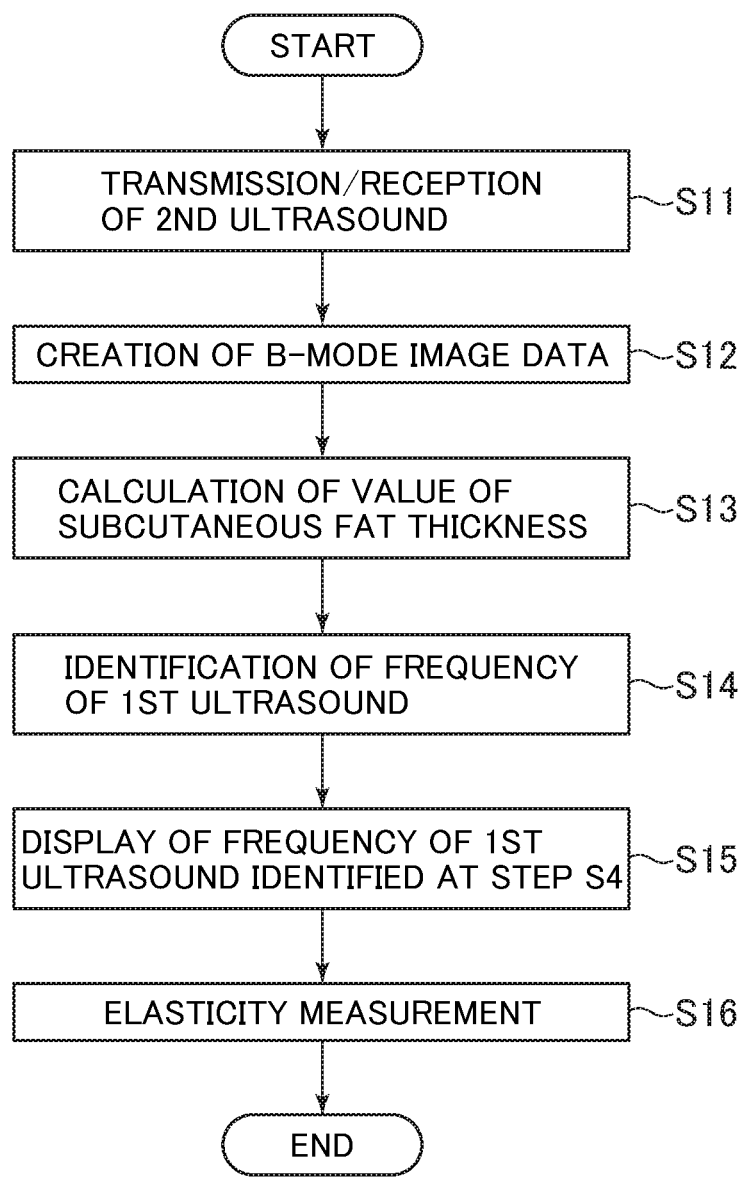
FIG. 8 is a flow chart showing an operation of the ultrasonic diagnostic apparatus in a first variation of the first embodiment.
Figure 9:
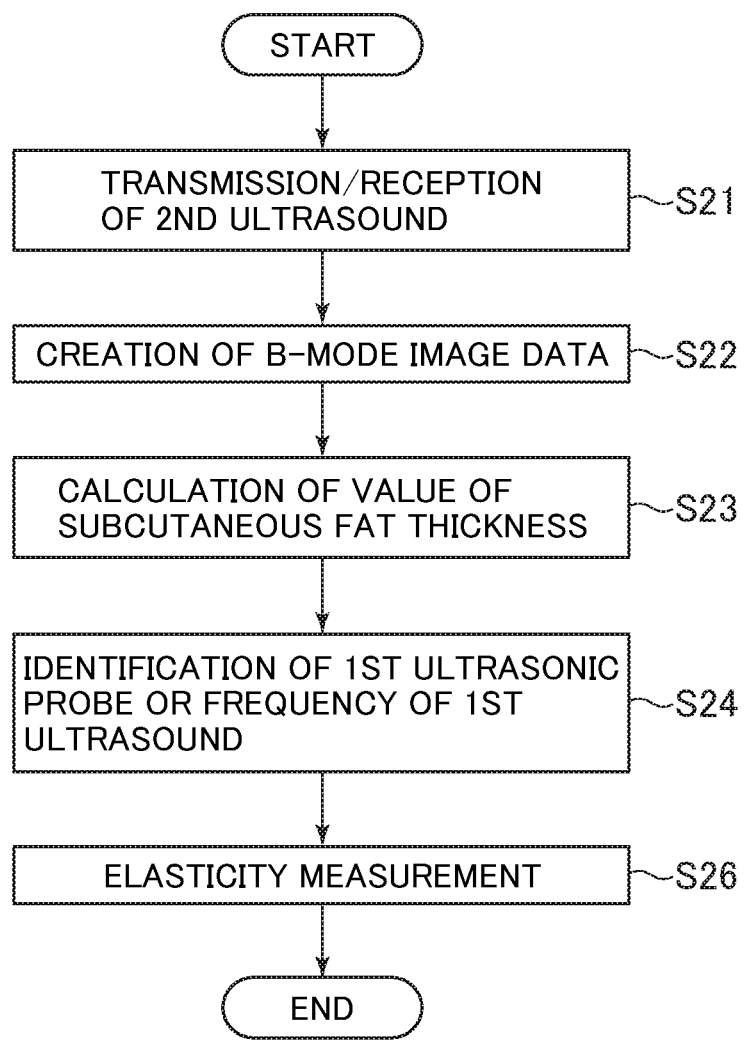
FIG. 9 is a flow chart showing an operation of the ultrasonic diagnostic apparatus in a second variation of the first embodiment.

Next, a second variation will be described. FIG. 9 is a flow chart showing an operation of the ultrasonic diagnostic apparatus in the second variation. Steps S21 to S23 shown in FIG. 8 are identical to Steps S1 to S3 and Steps S11 to S13, description of which will be omitted. At Step S24, the identifying section 82 identifies one first ultrasonic probe 21 from among the first ultrasonic probes 21A, 21B, 21C in a way similar to Step S4, or identifies a frequency of the first ultrasound in a way similar to Step S14.

Once the first ultrasonic probe 21 or the frequency of the first ultrasound has been identified at Step S24, the flow goes to processing at Step S26. At Step S26, elasticity measurement is performed. In the elasticity measurement at Step S26, the T/R control section 101 transmits first ultrasound by the first ultrasonic probe 21 identified at Step S24. Alternatively, in the case that the frequency of the first ultrasound is identified at Step S24, the first ultrasound is transmitted by a first ultrasonic probe 21 corresponding to the frequency. The T/R control section 101 is an exemplary embodiment of the control section in the present invention.

The T/R control section 101 may transmit the first ultrasound in response to the operation device 7 accepting an input by the operator, for example.

The elasticity measurement at Step S26 is identical to that at Steps S6 and S16 except the feature described above.

According to the second variation, the most suitable first ultrasonic probe 21 may be automatically selected to perform elasticity measurement.

Figure 10:
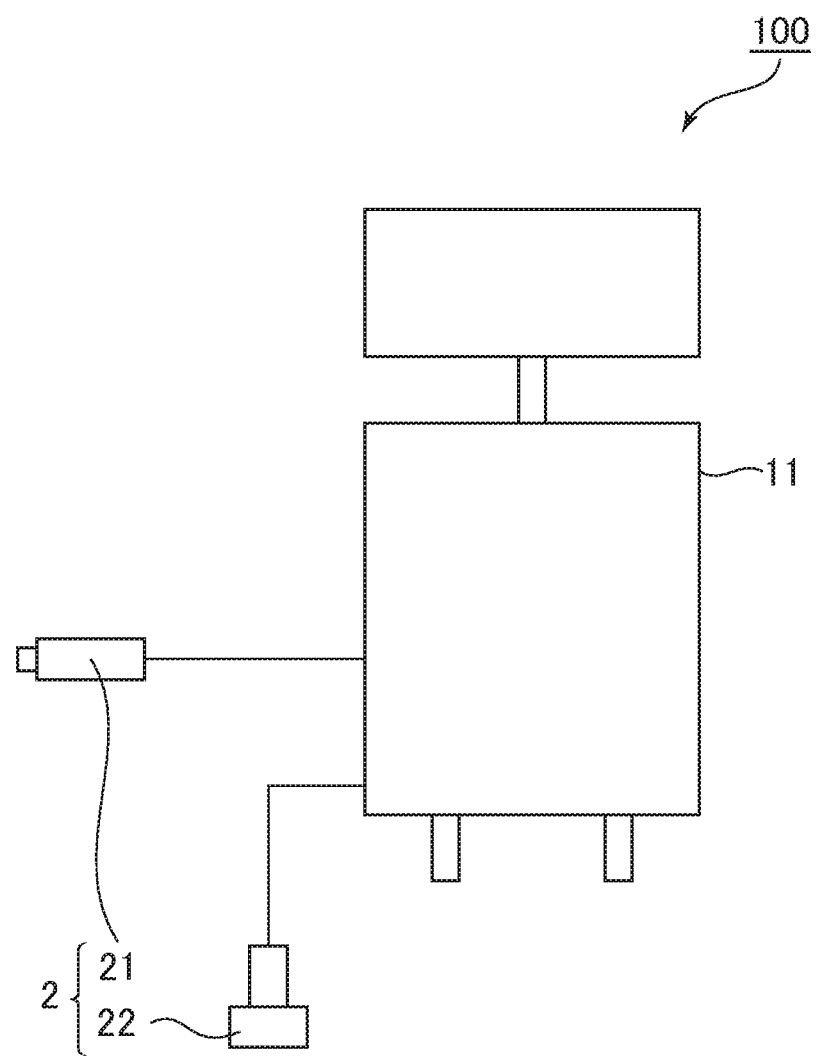
FIG. 10 is a diagram showing an outline of a third variation of the ultrasonic diagnostic apparatus constituting the ultrasonic diagnostic system in the first embodiment.

Next, a third variation will be described. As shown in FIG. 10, an ultrasonic diagnostic apparatus 11 in the third variation is connected with one first ultrasonic probe 21. The first ultrasonic probe 21 is configured to be capable of performing transmission/reception of a plurality of kinds of first ultrasound having different frequencies. The configuration of other components in the ultrasonic diagnostic apparatus 11 is identical to the ultrasonic diagnostic apparatus 1 shown by the block diagram in FIG. 3.

In the ultrasonic diagnostic apparatus 11, basically the same processing as that of the flow chart shown in FIG. 8, for example, is performed. However, at Step S14, the identifying section 82 identifies one frequency from among three different frequencies F1, F2, F3, for example, for the frequency of the first ultrasound based on the value of the subcutaneous fat thickness obtained at Step S13. It should be noted that identification of one frequency is not limited to that from among three frequencies F1, F2, F3.

At Step S16, the operator inputs a frequency displayed at Step S15 to the operation device 7. The inputting of a frequency may be an inputting of selection from among preset frequencies. The transmission control section 101 transmits first ultrasound of the frequency input at the operation device 7 by the first ultrasonic probe 21.

Moreover, basically the same processing as that of the flow chart shown in FIG. 9 may be performed in the ultrasonic diagnostic apparatus 11. However, since the present embodiment has a single first ultrasonic probe 21, the identifying section 82 identifies a frequency of the first ultrasound at Step S24, rather than identifying a first ultrasonic probe 21. At Step S26, the transmission control section 101 transmits first ultrasound of the frequency identified at Step S24 by the first ultrasonic probes 21.

Next, a second embodiment will be described. For components having identical symbols to those in the first embodiment, identical description to that in the first embodiment will be referred to, detailed description of which will be omitted.

Figure 11:
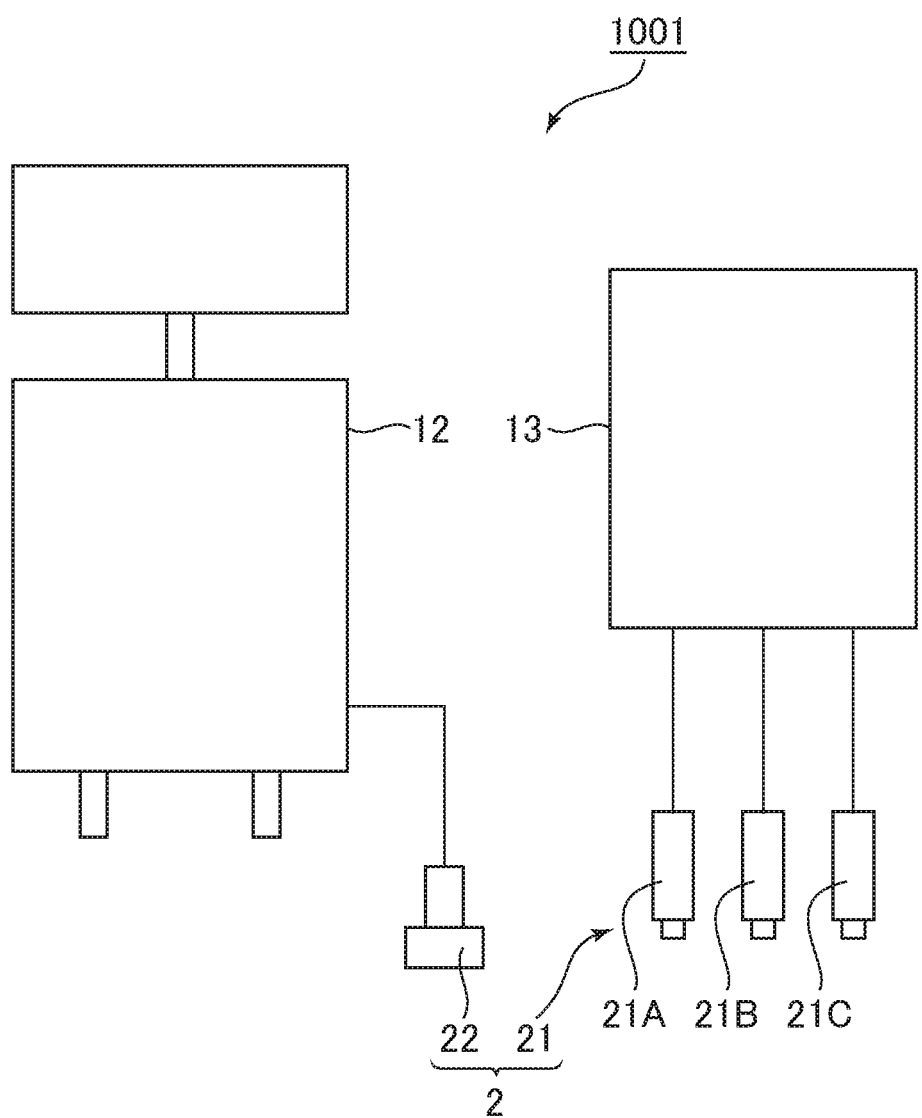
FIG. 11 is a diagram showing an outline of an exemplary ultrasonic diagnostic system in a second embodiment of the present invention.

An ultrasonic diagnostic system 1001 in the second embodiment shown in FIG. 11 is comprised of an ultrasonic diagnostic apparatus 12 and a measurement apparatus 13. The ultrasonic diagnostic apparatus 12 is connected with a second ultrasonic probe 22. The measurement apparatus 13 is connected with first ultrasonic probes 21A, 21B, 21C. The ultrasonic diagnostic apparatus 12 is an exemplary embodiment of the second apparatus in the present invention. The measurement apparatus 13 is an exemplary embodiment of the first apparatus in the present invention.

Figure 12:
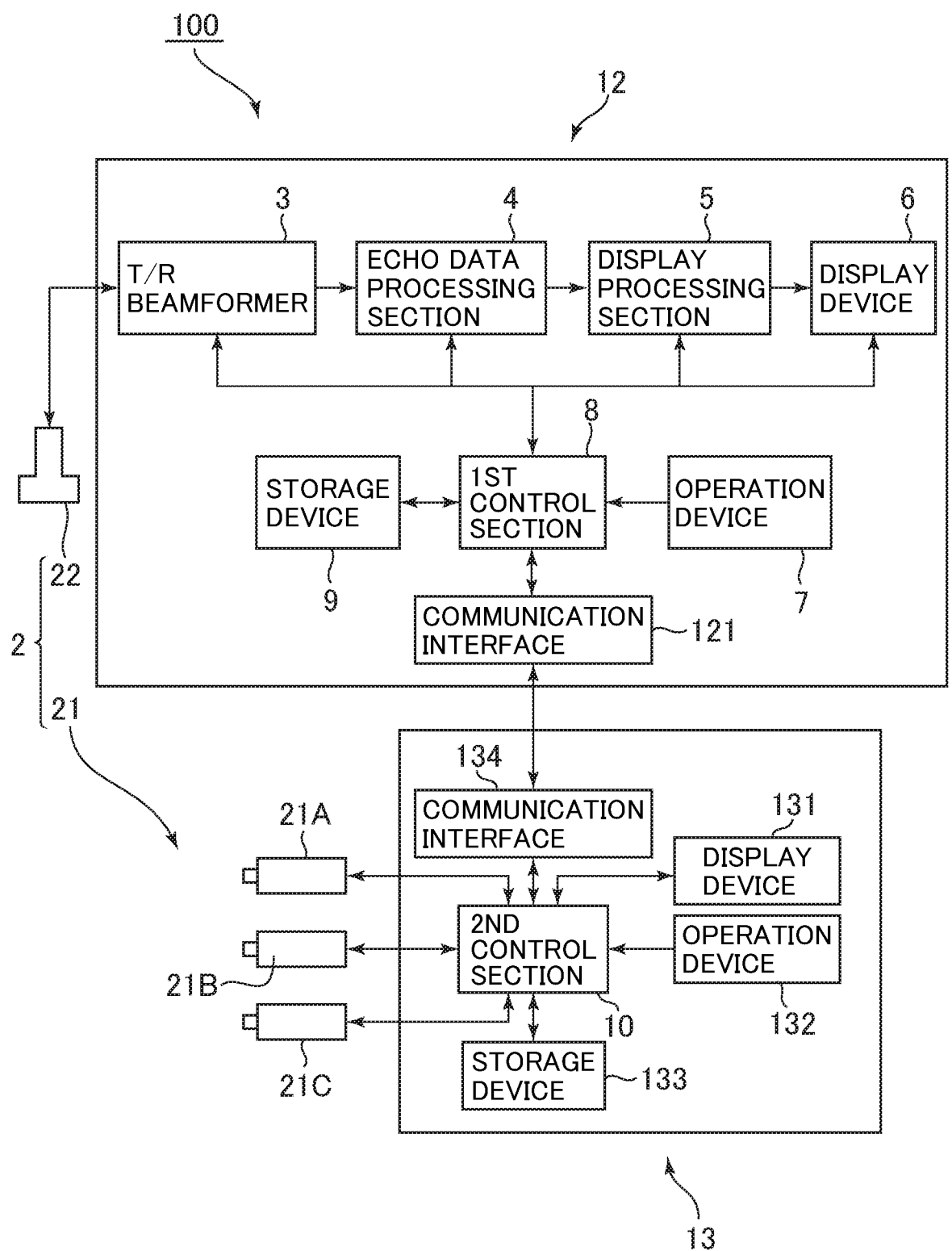
FIG. 12 is a block diagram showing a general configuration of the ultrasonic diagnostic apparatus and measurement apparatus constituting the ultrasonic diagnostic system shown in FIG. 11.

In addition to the second ultrasonic probe 22, the ultrasonic diagnostic apparatus 12 comprises, as shown in FIG. 12, the T/R beamformer 3, echo data processing section 4, display processing section 5, display device 6, operation device 7, first control section 8, storage device 9, and a communication interface 121. The measurement apparatus 13 comprises, in addition to the first ultrasonic probes 21A, 21B, 21C, the second control section 10, a display device 131, an operation device 132, a storage device 133, and a communication interface 134. The ultrasonic diagnostic apparatus 12 and measurement apparatus 13 are configured to be capable of communicating signals or the like to each other via the communication interfaces 121, 134.

Next, an operation of the ultrasonic diagnostic system 1001 in the present embodiment will be described. In the ultrasonic diagnostic system 1001 in the present embodiment, basically the same processing as that of the flow chart shown in FIG. 7 is performed. However, upon display of the characters or geometric shape indicating a first ultrasonic probe 21 on the display device 6 in the ultrasonic diagnostic apparatus 12 at Step S5, the operator performs an input of selecting the displayed first ultrasonic probe 21 at the operation device 132 in the measurement apparatus 13 at Step S6. The elasticity measurement described earlier is then performed.

It should be noted that in the present embodiment, information indicating the first ultrasonic probe 21 identified at the identifying section 82 may be transmitted to the measurement apparatus 13, and characters or a geometric shape indicating the first ultrasonic probe 21 may be displayed on the display device 131.

The ultrasonic diagnostic system 1001 in the present embodiment described above has the same effect as that in the first embodiment.

Next, variations of the second embodiment will be described. Now a first variation will be described first. The first variation is basically the same as the first variation in the first embodiment, and basically the same processing as that of the flow chart shown in FIG. 8 is performed. However, upon display of the frequency on the display device 6 in the ultrasonic diagnostic apparatus 12 at Step S15, an input of selecting a first ultrasonic probe 21 that transmits first ultrasound of the displayed frequency is performed at the operation device 132 at Step S16.

It should be noted that information indicating the frequency identified at the identifying section 82 may be transmitted to the measurement apparatus 13, and the frequency may be displayed on the display device 131.

Next, a second variation will be described. The second variation is basically the same as the second variation of the first embodiment, and basically the same processing as that of the flow chart shown in FIG. 9 is performed. However, at Step S26, a signal indicating a first ultrasonic probe 21 or a signal indicating a frequency of the first ultrasound identified at Step S24 is transmitted from the ultrasonic diagnostic apparatus 12 to the measurement apparatus 13. The T/R control section 101 transmits first ultrasound by the first ultrasonic probe 21 transmitted from the ultrasonic diagnostic apparatus 12. Alternatively, the T/R control section 101 transmits first ultrasound by a first ultrasonic probe 21 corresponding to the frequency transmitted from the ultrasonic diagnostic apparatus 12.

Figure 13:
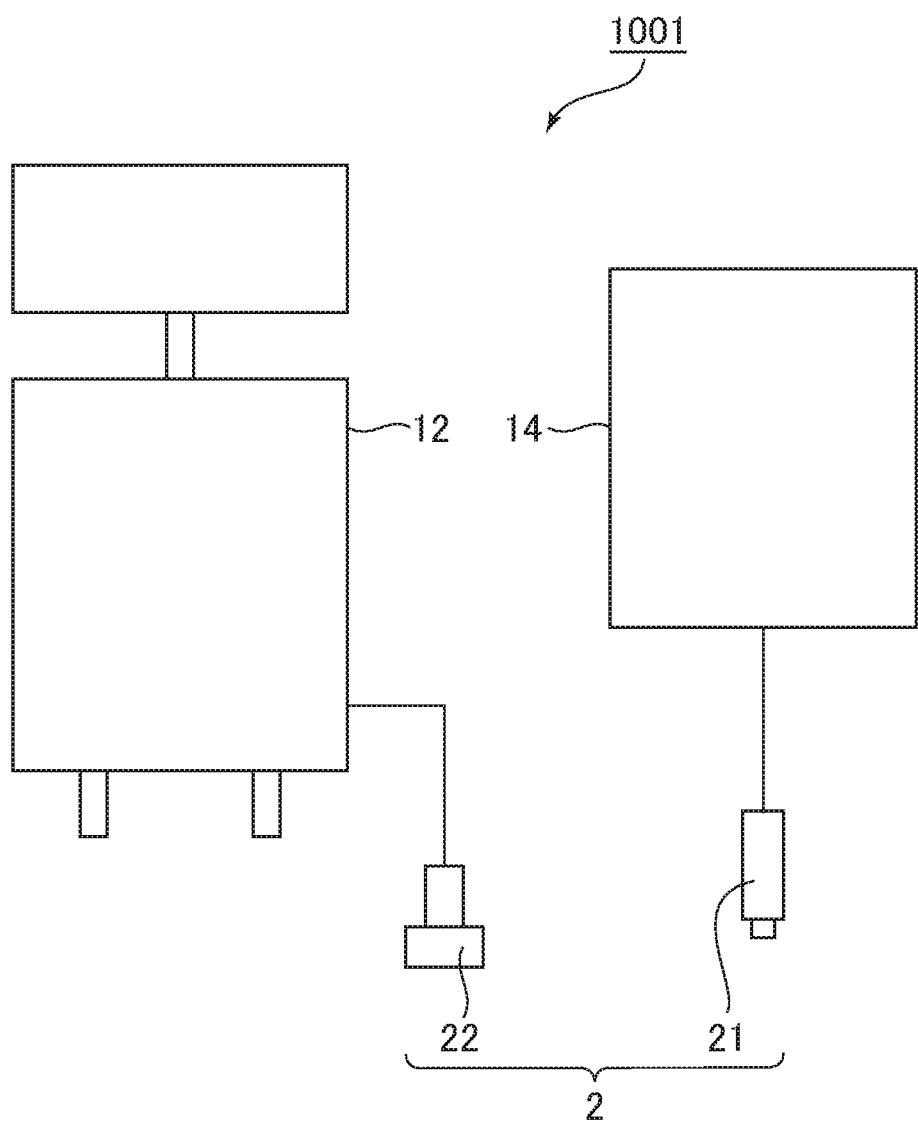
FIG. 13 is a diagram showing an outline of a third variation of the ultrasonic diagnostic system in the second embodiment of the present invention.

Next, a third variation will be described. As shown in FIG. 13, a measurement apparatus 14 in the third variation is connected with one first ultrasonic probe 21. The configuration of other components in the measurement apparatus 14 is identical to the measurement apparatus 13 shown by the block diagram in FIG. 12.

In the ultrasonic diagnostic system 1001 in the third variation, again, the same processing as that of the flow chart shown in FIG. 8 is performed. However, the operator inputs the frequency displayed at Step S15 at the operation device 132 in the measurement apparatus 14. Thus, first ultrasound of the input frequency is transmitted.

Alternatively, in the ultrasonic diagnostic system 1001 in the third variation, basically the same processing as that of the flow chart shown in FIG. 9 may be performed. However, since the present embodiment has a single first ultrasonic probe 21, the identifying section 82 identifies a frequency of the first ultrasound at Step S24, rather than identifying a first ultrasonic probe 21. At Step S26, a signal indicating the frequency identified at Step S24 is transmitted from the ultrasonic diagnostic apparatus 12 to the measurement apparatus 14. The T/R control section 101 then transmits first ultrasound of the frequency transmitted from the ultrasonic diagnostic apparatus 12 by the first ultrasonic probe 21.

Next, a third embodiment will be described. For components having identical symbols to those in the first and second embodiments, identical description to that in the first and second embodiments will be referred to, detailed description of which will be omitted.

Figure 14:
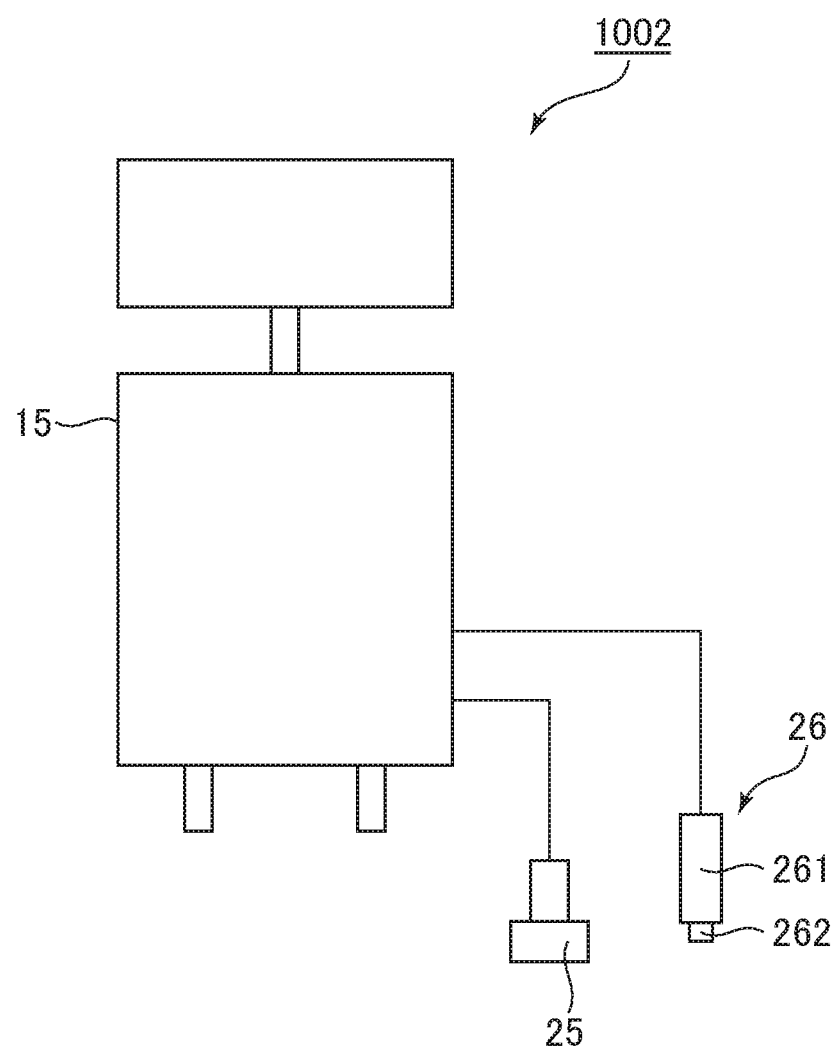
FIG. 14 is a diagram showing an outline of an exemplary ultrasonic diagnostic apparatus constituting an ultrasonic diagnostic system in a third embodiment of the present invention.

An ultrasonic diagnostic system 1002 in the third embodiment shown in FIG. 14 is comprised of an ultrasonic diagnostic apparatus 15. The ultrasonic diagnostic apparatus 15 is connected with an ultrasonic probe 25 and a vibrator 26. The ultrasonic probe 25 has a plurality of ultrasonic transducers arranged in an azimuthal direction. The ultrasonic probe 25 performs transmission/reception of the first ultrasound and transmission/reception of the second ultrasound to/from a subject. The ultrasonic probe 25 is configured, again in the present embodiment, to be capable of transmitting ultrasound of different frequencies as the first ultrasound. The ultrasonic probe 25 is an exemplary embodiment of the transceiver in the present invention.

The vibrator 26 has a main body portion 261, and a cylindrical protrusion 262 provided at the tip. The protrusion 262 is configured to axially reciprocate with respect to the main body portion 261. It is by the axially moving protrusion 262 that mechanical vibration is applied to the subject. Shear waves generated within biological tissue in the subject by the mechanical vibration applied by the protrusion 262 are detected by the first ultrasound. The vibrator 26 is an exemplary embodiment of the vibrator in the present invention.

It should be noted that no ultrasonic transducer is provided in the protrusion 262.

Figure 15:
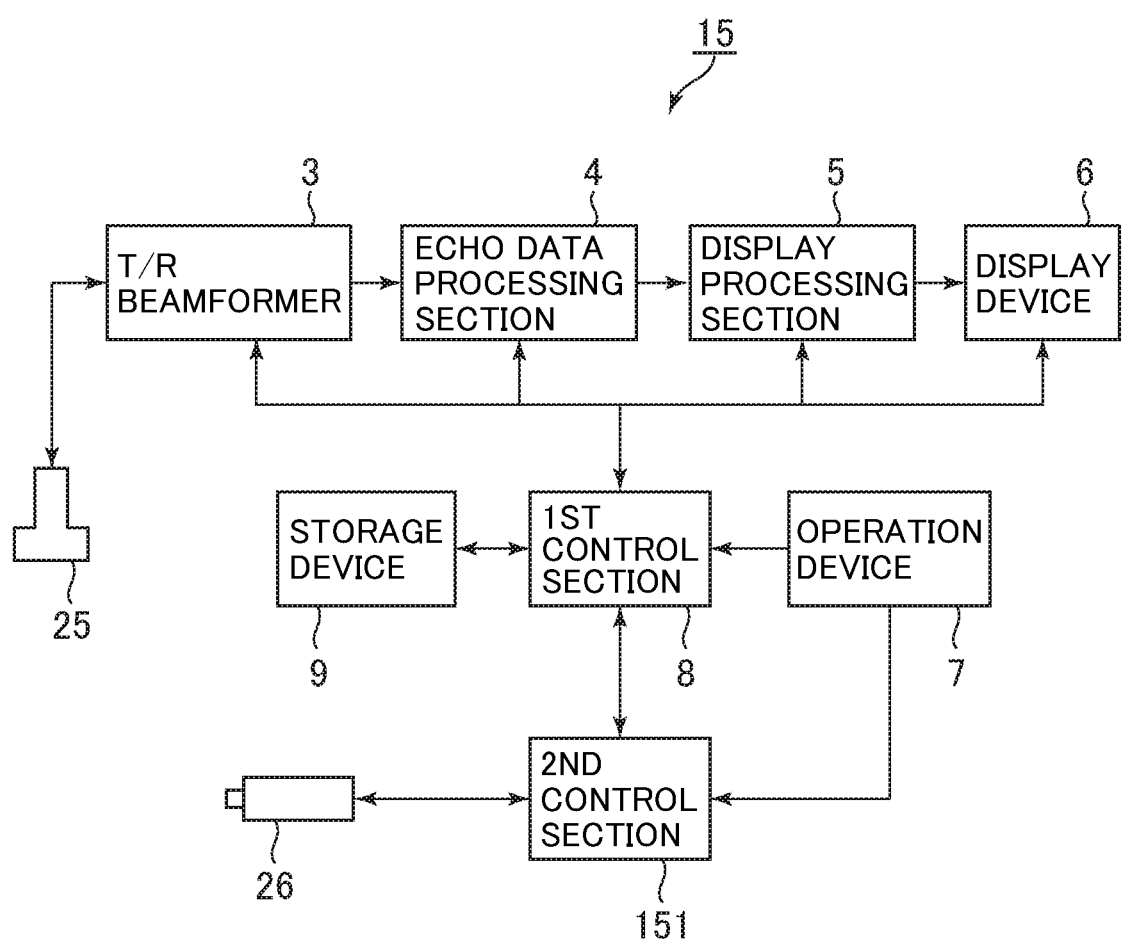
FIG. 15 is a block diagram showing a general configuration of the ultrasonic diagnostic apparatus shown in FIG. 14.

A block configuration of the ultrasonic diagnostic apparatus 15 will be described with reference to FIG. 15. In addition to the ultrasonic probe 25 and vibrator 26, the ultrasonic diagnostic apparatus 15 comprises the T/R beamformer 3, echo data processing section 4, display processing section 5, display device 6, operation device 7, first control section 8, and storage device 9, as in the ultrasonic diagnostic apparatus 1 in the first embodiment. The ultrasonic diagnostic apparatus 15 also comprises a second control section 151.

In the present embodiment, the T/R beamformer 3 drives the ultrasonic probe 25 based on a control signal from the first control section 8 to transmit first ultrasound, in addition to second ultrasound. The first ultrasound may be transmitted using a single ultrasonic transducer or a plurality of ultrasonic transducers. The ultrasonic probe 25 is configured to be capable of performing transmission/reception of a plurality of kinds of first ultrasound having different frequencies.

Figure 16:
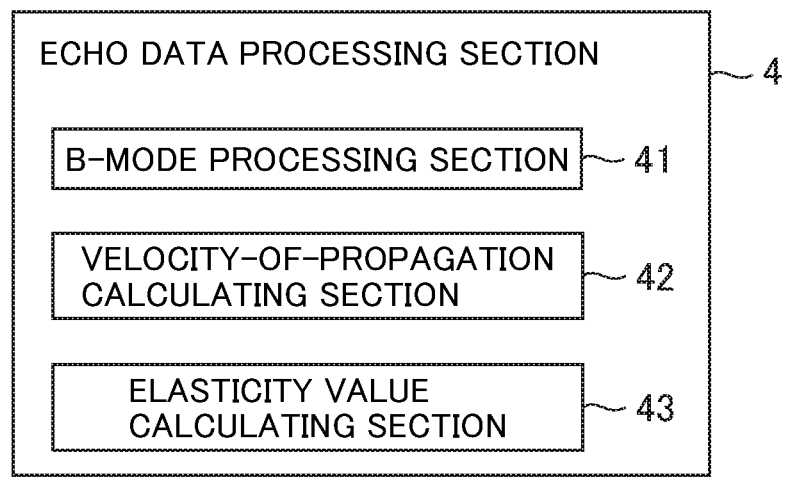
FIG. 16 is a block diagram showing a configuration of an echo data processing section in the ultrasonic diagnostic apparatus shown in FIG. 15.

In the present embodiment, the echo data processing section 4 has a B-mode processing section 41, a velocity-of-propagation calculating section 42, and an elasticity-value calculating section 43, as shown in FIG. 16. The B-mode processing section 41 performs B-mode processing to create B-mode data. The velocity-of-propagation calculating section 42 calculates a velocity of propagation of the shear waves described above based on echo signals from the first ultrasound received at the ultrasonic probe 25, as with the velocity-of-propagation calculating section 103. The elasticity-value calculating section 43 calculates an elasticity value based on the velocity of propagation, as with the elasticity-value calculating section 104.

Figure 17:
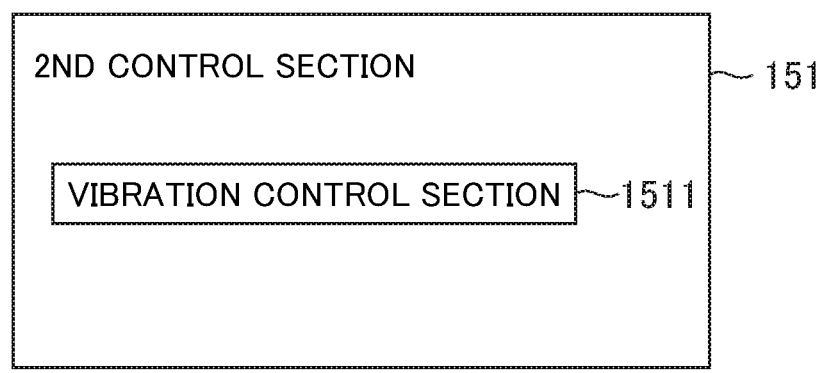
FIG. 17 is a block diagram showing an exemplary function executed by a second control section in the ultrasonic diagnostic apparatus shown in FIG. 15.

The second control section 151 has a vibration control section 1511, as shown in FIG. 17. The vibration control section 1511 controls the operation of the vibrator 26.

Next, an operation of the ultrasonic diagnostic system 1002 in the present embodiment will be described. In the ultrasonic diagnostic system 1002 in the present embodiment, basically the same processing as that of the flow chart shown in FIG. 8 is performed. However, at Step S11, the ultrasonic probe 25 performs transmission/reception of the second ultrasound.

Moreover, at Step S14, the identifying section 82 identifies one frequency from among three different frequencies F1, F2, F3, for example, as the frequency for the first ultrasound based on the value of the subcutaneous fat thickness obtained at Step S13. Furthermore, at Step S16, the operator inputs the frequency displayed at Step S15 at the operation device 7, as in the third variation of the first embodiment. The operator also puts the vibrator 26 against the body surface of the subject. Under these conditions, the second control section 151 drives the vibrator 212, which applies mechanical vibration to biological tissue. To the first control section 8 is input a signal indicating that the vibrator 212 is driven from the second control section 151. Once the signal has been input to the first control section 8, it outputs a signal for driving the ultrasonic probe 25 and transmits first ultrasound of the frequency input at the operation device 7 from the ultrasonic probe 25.

The present embodiment described above, again, has the same effect as those in the first and second embodiments.

Next, variations of the third embodiment will be described. Now a first variation will be described first. In the first variation, basically the same processing as that of the flow chart shown in FIG. 9 is performed. However, at Step S24, the identifying section 82 identifies a frequency of the first ultrasound. At Step S26, once the operation device 7 has accepted an input by the operator, for example, the second control section 151 drives the vibrator 26. Moreover, upon an input of a signal indicating that the vibrator 26 has been driven from the second control section 151, the first control section 8 outputs a signal for driving the ultrasonic probe 25 to transmit therefrom first ultrasound of the frequency input at the operation device 7. In the present embodiment, the first control section 8 is an exemplary embodiment of the control section in the present invention.

Figure 18:
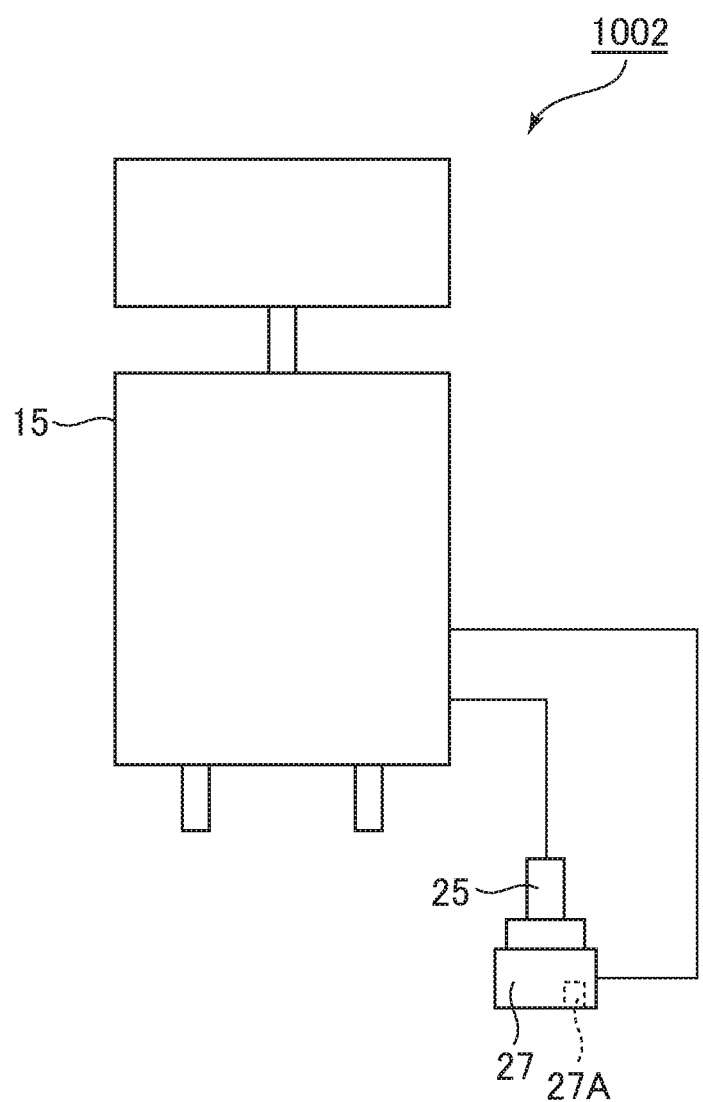
FIG. 18 is a diagram showing an outline of a second variation of the ultrasonic diagnostic system in the third embodiment.

Next, a second variation will be described. In the ultrasonic diagnostic apparatus 15 in the second variation shown in FIG. 18, a vibrator 27 is attached to the ultrasonic probe 25 in a removable manner The vibrator 27 has the same configuration as that of an attachment disclosed in Japanese Patent Application KOKAI No. 2015-039583, and it is by an axially moving vibrating section 27A that mechanical vibration is applied to a subject. The vibrating section 27A is controlled by the vibration control section 1511 in the second control section 151.

The operation of the second variation is similar to that of the third embodiment and that of the first variation of the third embodiment described above, description of which will be omitted.

Figure 19:
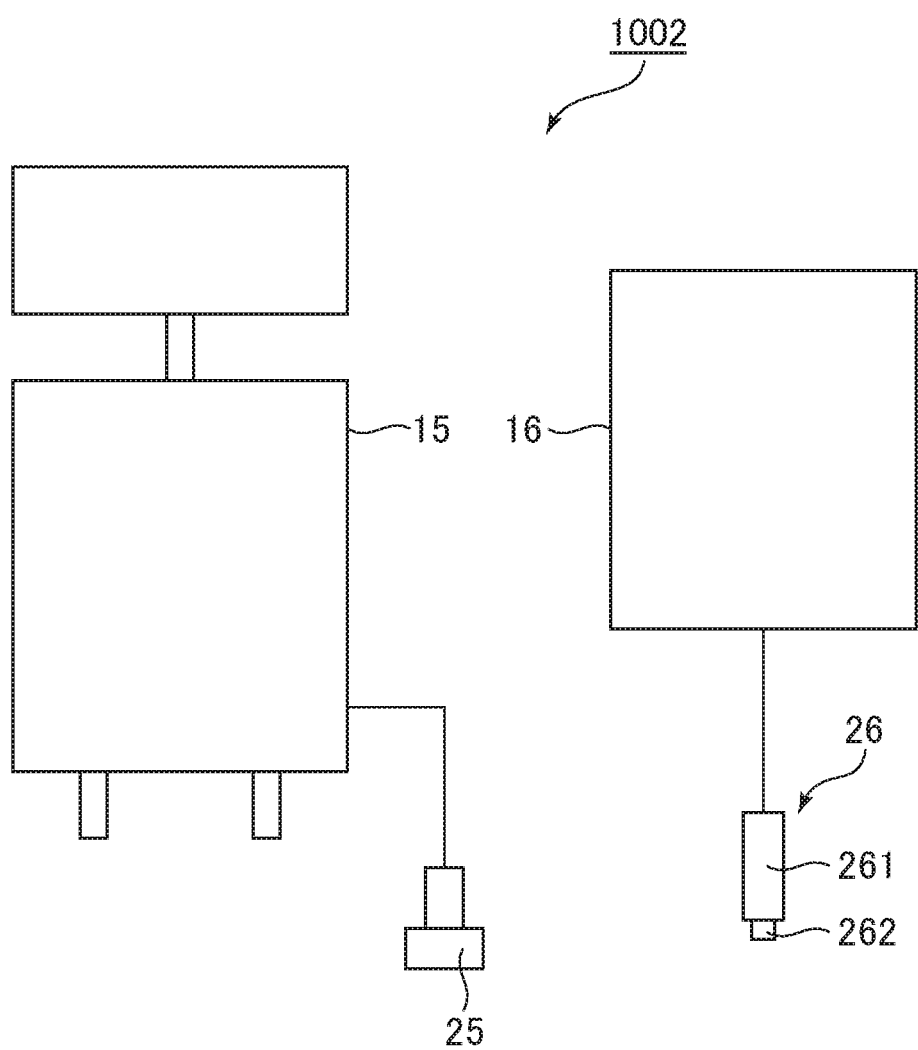
FIG. 19 is a diagram showing an outline of a third variation of the ultrasonic diagnostic system in the third embodiment.

Next, a third variation will be described. As shown in FIG. 19, an ultrasonic diagnostic system 1002 in the third variation is comprised of the ultrasonic diagnostic apparatus 15 and a vibration apparatus 16. The vibrator 26 is connected to the vibration apparatus 16, rather than to the ultrasonic diagnostic apparatus 15. In the present embodiment, the vibration apparatus 16 is an exemplary embodiment of the first apparatus, and the ultrasonic diagnostic apparatus 15 is an exemplary embodiment of the second apparatus.

Figure 20:
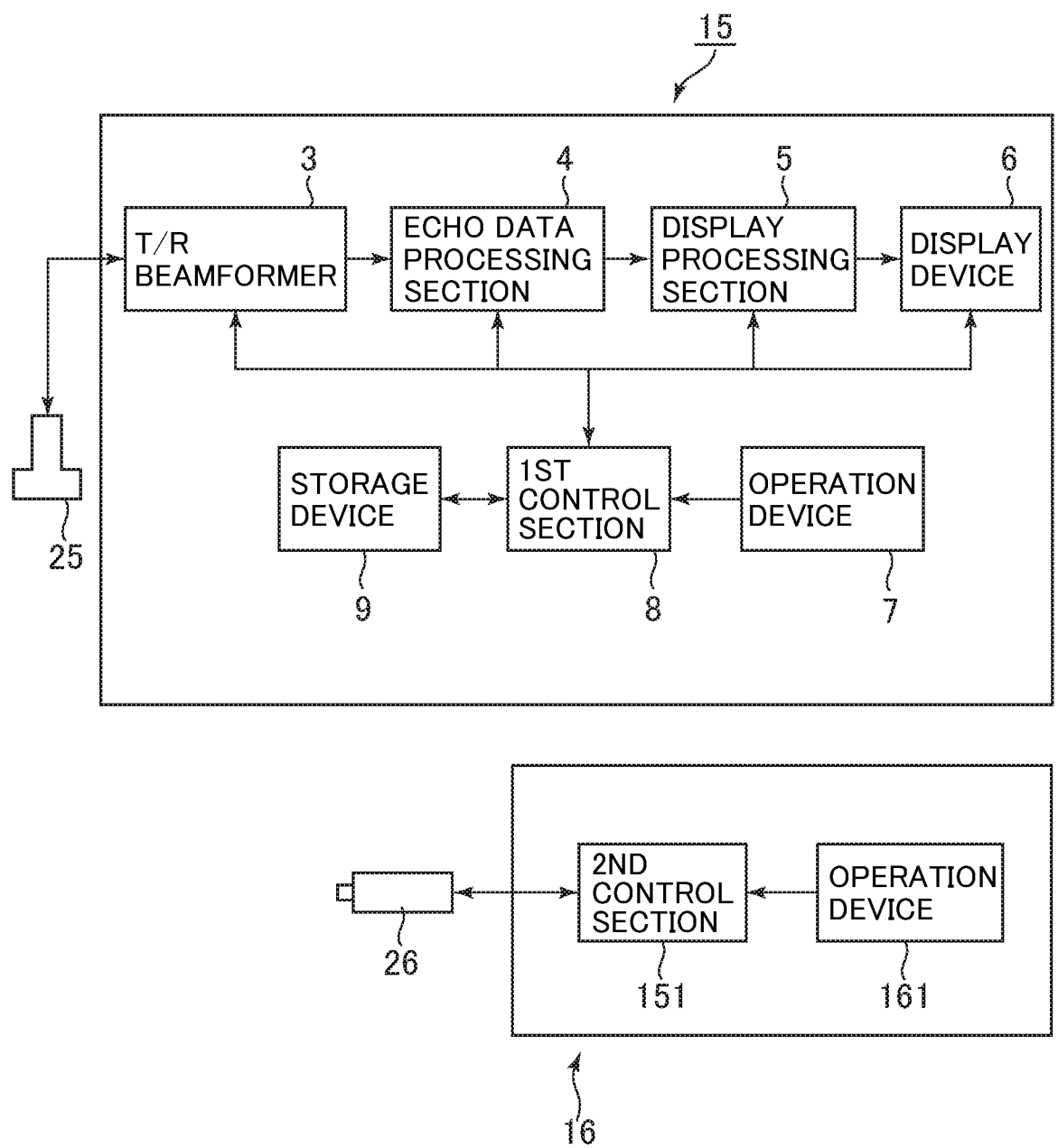
FIG. 20 is a block diagram showing a general configuration of the ultrasonic diagnostic apparatus and vibrator apparatus constituting the ultrasonic diagnostic system shown in FIG. 19.

The vibration apparatus 16 comprises the aforementioned second control section 151, as shown in FIG. 20. The vibration control section 1511 (FIG. 17) in the second control section 151 controls the operation of the vibrator 26. The vibration apparatus 16 also comprises an operation device 161. Once the operation device 161 has accepted an input by the operator, the vibration control section 1511 drives the vibrator 26.

It should be noted that the vibration apparatus 16 may comprise a display device and/or a storage device, although not particularly shown.

When the ultrasonic diagnostic apparatus 15 and vibration apparatus 16 are capable of communication, the vibrator 26 may be configured to be driven by a signal transmitted from the first control section 8.

The configuration of the ultrasonic diagnostic apparatus 15 is identical to those described earlier.

The operation of the third variation, again, is similar to that of the third embodiment and that of the first variation of the third variation, description of which will be omitted.

In the present embodiment, the ultrasonic diagnostic apparatus 15 may be connected with the first ultrasonic probe(s) 21 and second ultrasonic probe 22, in place of the ultrasonic probe 25. As the first ultrasonic probe(s) 21, a plurality of the first ultrasonic probes 21 or a single first ultrasonic probe 21 may be connected.

Figure 21:
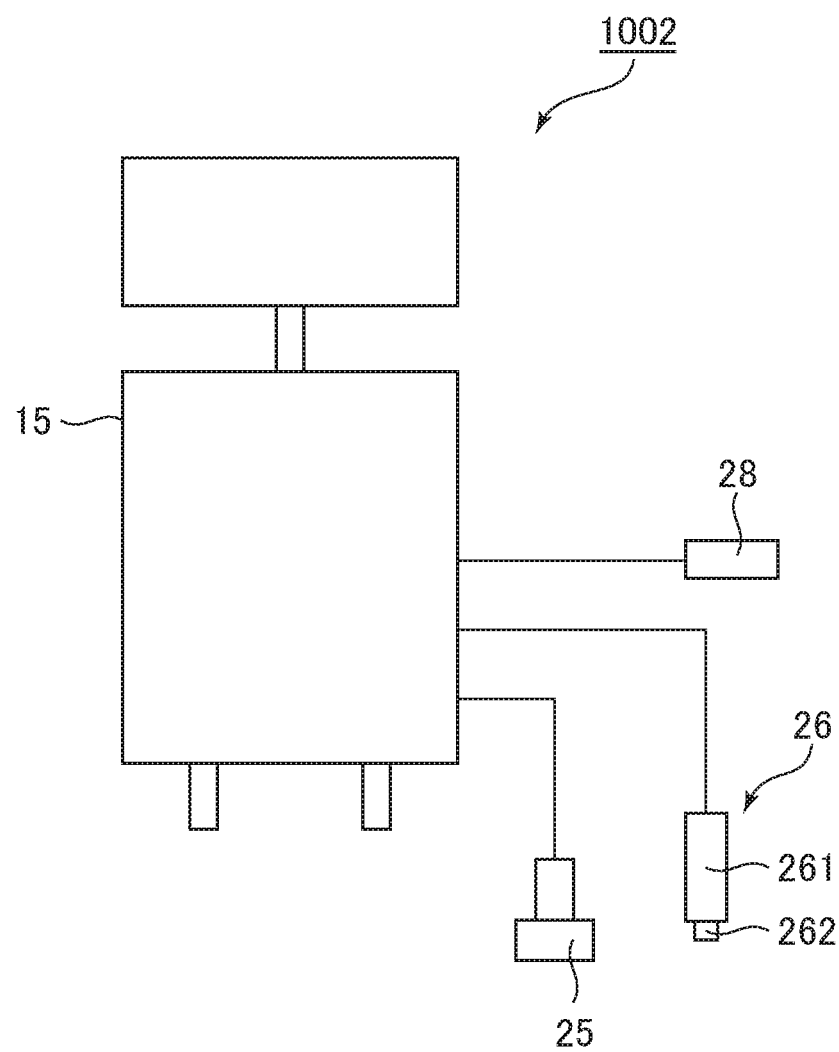
FIG. 21 is a diagram showing an outline of a fourth variation of the ultrasonic diagnostic system in the third embodiment of the present invention.

Next, a fourth variation will be described. As shown in FIG. 21, in addition to the ultrasonic probe 25, an ultrasonic probe 28 for transmitting first ultrasound is connected to the ultrasonic diagnostic apparatus 15. In the fourth variation, the ultrasonic probe 25 does not perform transmission/reception of the first ultrasound but does perform only transmission/reception of the second ultrasound. In the fourth variation, the ultrasonic probe 25 is an exemplary embodiment of the second transceiver, and the ultrasonic probe 28 is an exemplary embodiment of the first transceiver.

The ultrasonic probe 28 performs transmission/reception of the first ultrasound based on a control signal from the first control section 8. The ultrasonic probe 28 is configured to be capable of transmitting/receiving a plurality of kinds of first ultrasound having different frequencies.

The operation of the fourth variation is basically the same as that of the third embodiment and that of the first variation of the third embodiment described above, except that the first ultrasound is transmitted from the ultrasonic probe 28.

Figure 22:
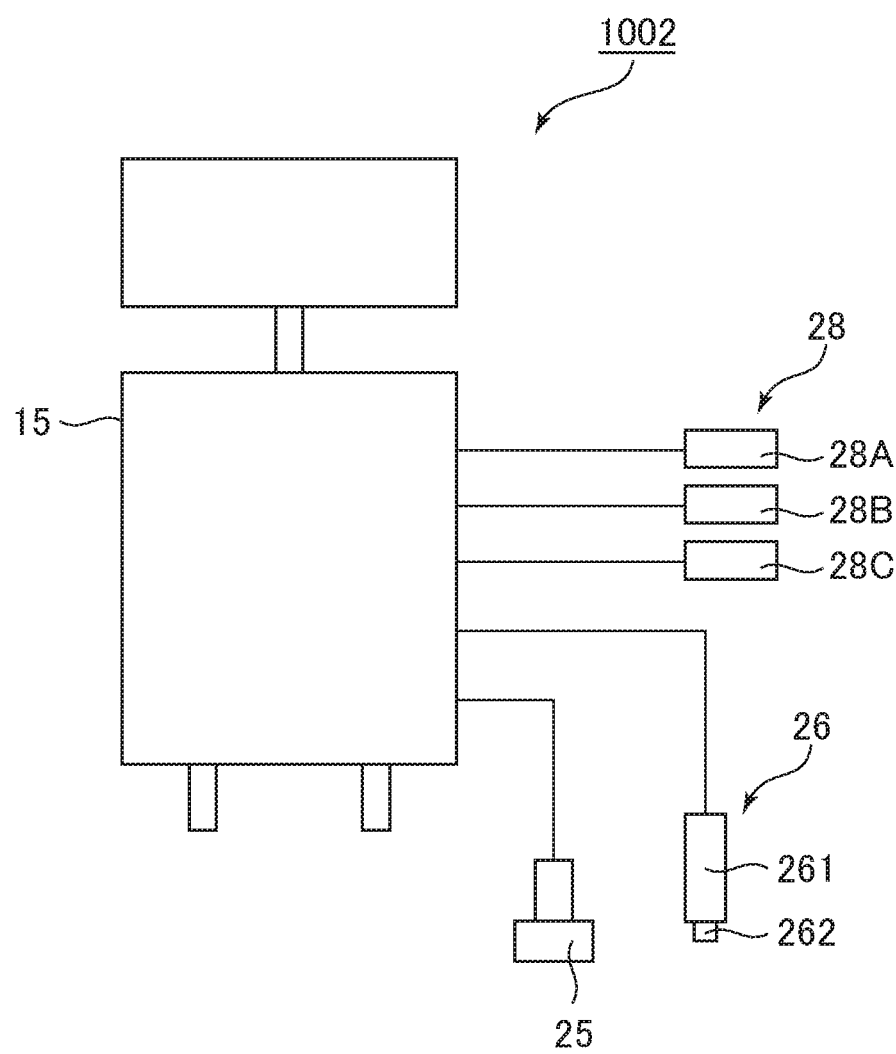
FIG. 22 is a diagram showing an outline of a fifth variation of the ultrasonic diagnostic system in the third embodiment of the present invention.

Next, a fifth variation will be described. As shown in FIG. 22, three ultrasonic probes 28A, 28B, 28C may be connected to the ultrasonic diagnostic apparatus 15 as the ultrasonic probes 28. The frequency of the first ultrasound to be transmitted/received by each of the ultrasonic probes 28A, 28B, 28C is different from probe to probe. One ultrasonic probe 28 of the ultrasonic probes 28A, 28B, 28C performs transmission/reception of the first ultrasound based on a control signal from the first control section 8.

The operation of the fifth variation is basically the same as that of the third embodiment and that of the first variation of the third embodiment described above, except that the first control section 8 drives one ultrasonic probe 28 of the ultrasonic probes 28A, 28B, 28C to perform transmission/reception of the first ultrasound.

Figure 7:
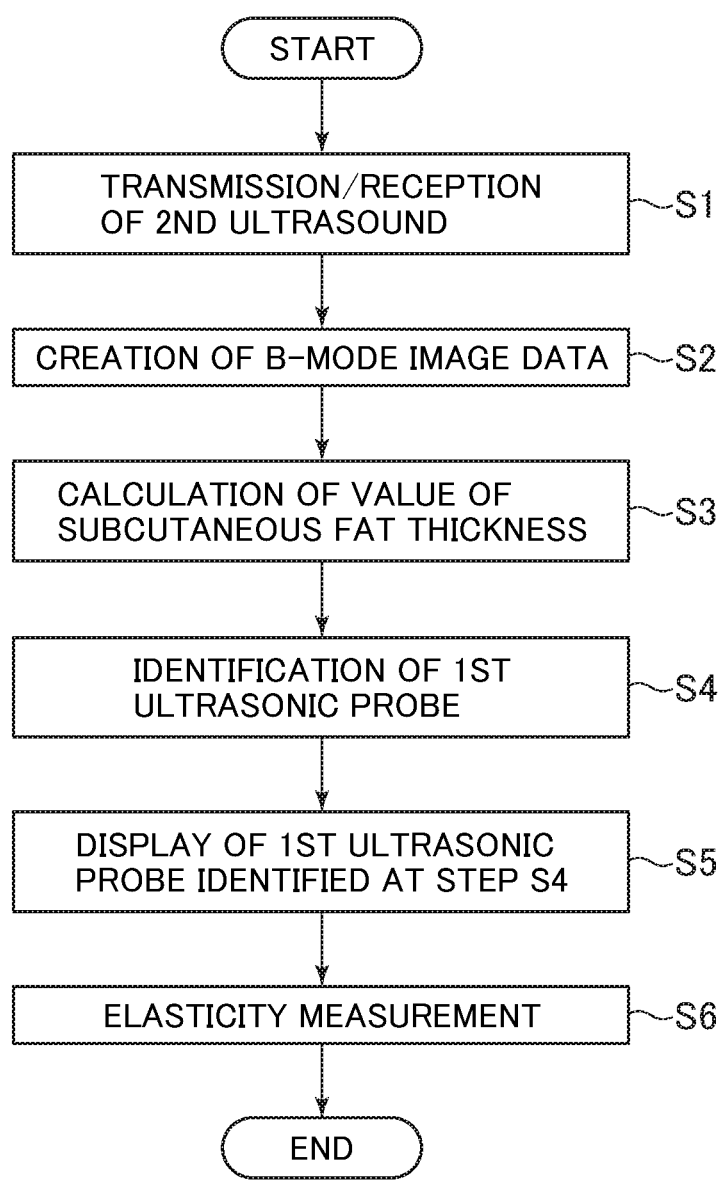
FIG. 7 is a flow chart showing an operation of the ultrasonic diagnostic apparatus in the first embodiment.

In the fifth variation, basically the same processing as that of the flow chart shown in FIG. 7 may also be performed. In this case, the operator performs an input of selecting one ultrasonic probe 28 of the ultrasonic probes 28A, 28B, 28C at the operation device 7. Transmission/reception of the first ultrasound is then performed by the selected ultrasonic probe 28.

Next, a fourth embodiment will be described. For components having identical symbols to those in the first, second, and third embodiments, identical description to that in the first, second, and third embodiments will be referred to, detailed description of which will be omitted.

Figure 23:
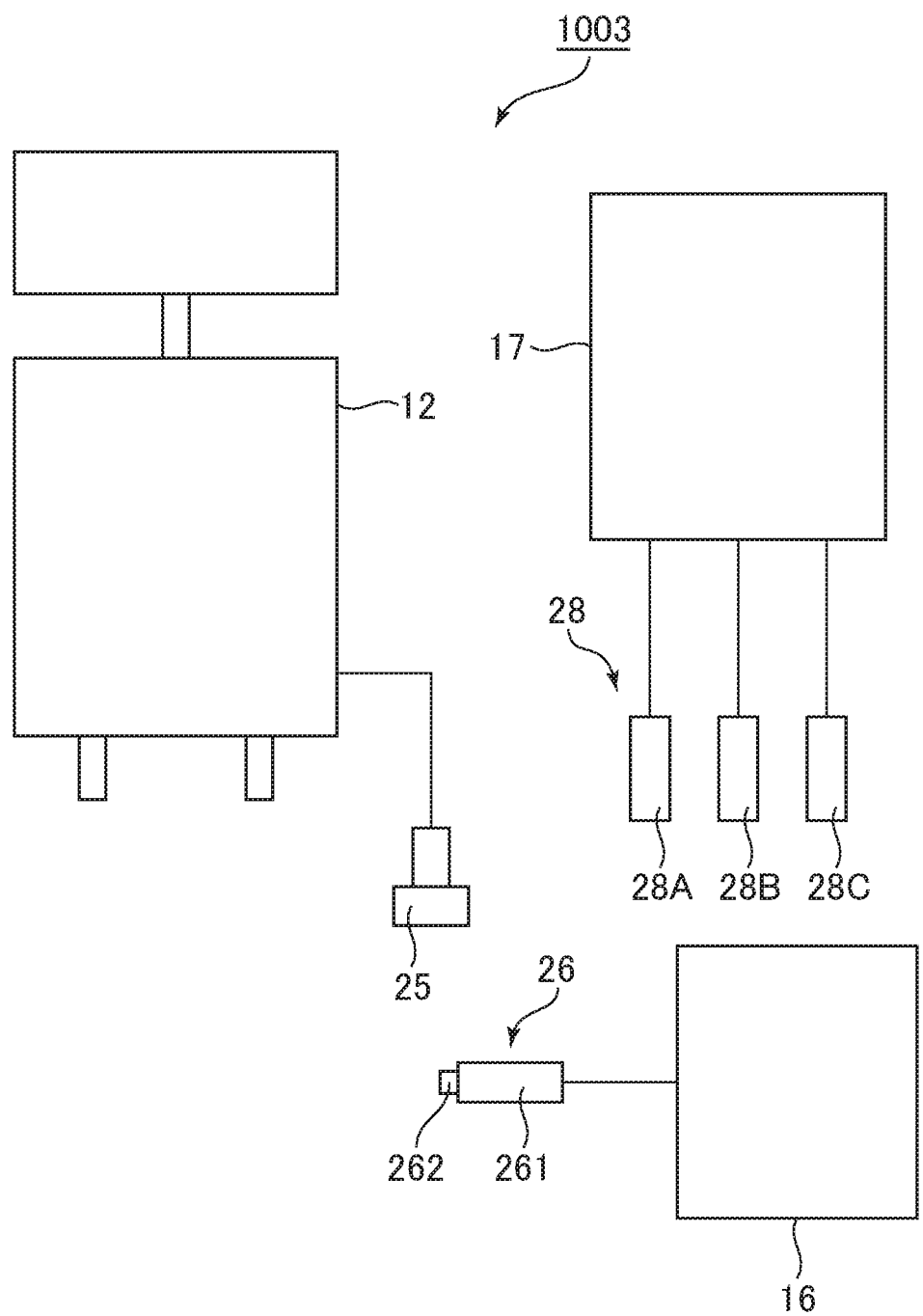
FIG. 23 is a diagram showing an outline of an exemplary ultrasonic diagnostic system in a fourth embodiment of the present invention.

An ultrasonic diagnostic system 1003 in the fourth embodiment shown in FIG. 23 is comprised of the ultrasonic diagnostic apparatus 12, a measurement apparatus 17, and the vibration apparatus 16. The ultrasonic diagnostic apparatus 12 is the one described in the second embodiment, and the vibration apparatus 16 is the one described in the third variation of the third embodiment. The measurement apparatus 17 has basically the same configuration as that of the measurement apparatus 13 described in the second embodiment. However, the measurement apparatus 17 is connected with the ultrasonic probes 28A, 28B, 28C. Moreover, the second control section 10 executes the functions except that of the vibration control section 102, i.e., the functions of the T/R control section 101, velocity-of-propagation calculating section 103, and elasticity-value calculating section 104.

In the present embodiment, the ultrasonic diagnostic apparatus 12 is an exemplary embodiment of the third apparatus in the present invention. In the present embodiment, the measurement apparatus 17 is an exemplary embodiment of the second apparatus in the present invention. In the present embodiment, the vibration apparatus 16 is an exemplary embodiment of the first apparatus in the present invention.

Now an operation of the present embodiment will be described. In the ultrasonic diagnostic system 1003 in the present embodiment, basically the same processing as that of the second embodiment is performed with reference to the flow charts shown in FIGS. 7, 8, and 9. However, the measurement apparatus 17 is used in the present embodiment in place of the measurement apparatus 13 in the second embodiment, and mechanical vibration is applied by the vibrator 26.

It should be noted that in the present embodiment, again, there may be a single ultrasonic probe 28, although not particularly shown.

While the present invention has been described with reference to the embodiments, it will be easily recognized that the present invention may be practiced with several modifications without changing the spirit and scope thereof. For example, the value of the parameter calculated by the computing section 81 is not limited to the value of the subcutaneous fat thickness. For example, the computing section 81 may calculate the amount of ultrasound attenuation in a subject based on echo signals from the second ultrasound as the value of the parameter described above. In this case, the computing section 81 may calculate a mean value of the amounts of attenuation in a plurality of acoustic lines in a B-mode image, for example, as the amount of ultrasound attenuation. Moreover, the computing section 81 may calculate an amount of attenuation of an echo signal from the second ultrasound in one acoustic line as the amount of ultrasound attenuation.

The frequency of the first ultrasound is lower for a greater amount of attenuation calculated by the computing section 81, while it is higher for a smaller amount of attenuation.

For example, attenuation in biological tissue is sometimes small in spite of thick subcutaneous fat. Therefore, by the frequency of the first ultrasound determined based on the amount of attenuation as described above, first ultrasound having a suitable frequency may be used in elasticity measurement.

Moreover, the computing section 81 may calculate a distance from the body surface to the diaphragm of a subject as the value of the parameter described above based on B-mode image data. The computing section 81 calculates a distance from the body surface to the diaphragm of a subject by performing image processing of extracting the diaphragm based on information indicating the brightness of B-mode image data, for example. The frequency of the first ultrasound is higher for a smaller distance calculated by the computing section 81.

For example, in the case that the distance from the body surface to the diaphragm of a subject is relatively small, when first ultrasound of lower frequency is transmitted, the first ultrasound may overpenetrate and may be reflected at the diaphragm in unexpected directions. Accordingly, by increasing the frequency of the first ultrasound for a smaller value of the distance calculated by the computing section 81, the problem of the reflection may be solved.

Figure 24:
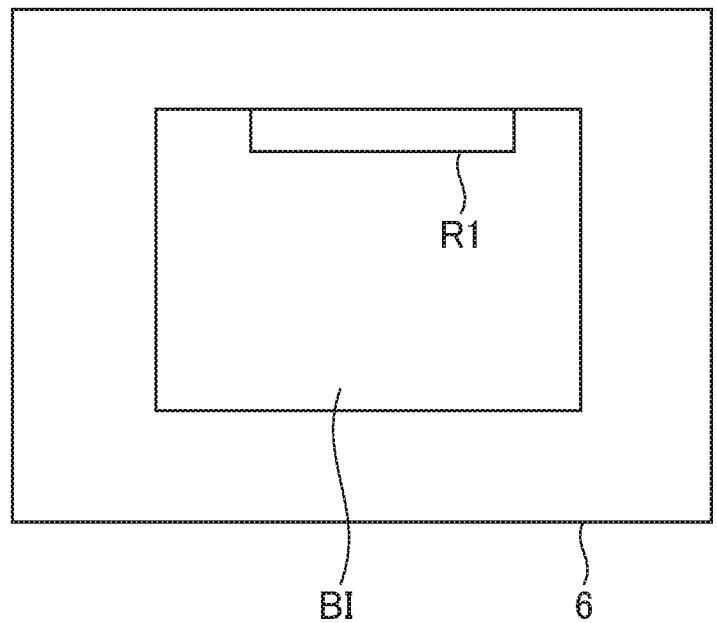
FIG. 24 is a diagram showing a display device on which a B-mode image is displayed, where the B-mode image has a geometric shape indicating a range for which a value of the subcutaneous fat thickness is to be calculated.

Moreover, as shown in FIG. 24, the display image control section 52 may display in a B-mode image BI displayed on the display device 6 a geometric shape R1 indicating a range for which the value of the subcutaneous fat thickness is to be calculated. In the present embodiment, the geometric shape R1 is a rectangle. However, the form of the geometric shape R1 is not limited to a rectangle. The display device 6 is an exemplary embodiment of the display device in the present invention.

Figure 25:
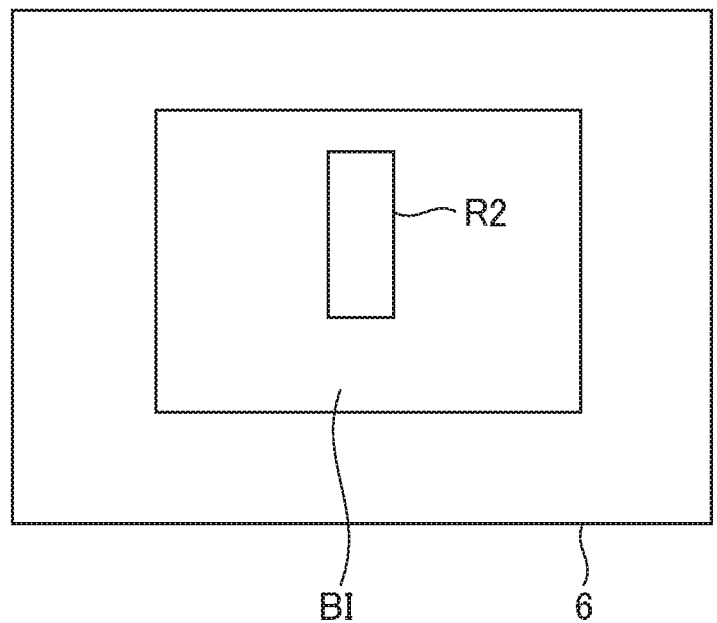
FIG. 25 is a diagram showing a display device on which a B-mode image is displayed, where the B-mode image has a geometric shape indicating a range for which a velocity-of-propagation is to be calculated.

Furthermore, as shown in FIG. 25, the display image control section 52 may display in the B-mode image BI displayed on the display device 6 a geometric shape R2 indicating a range for which the velocity of propagation is to be calculated by the velocity-of-propagation calculating section 42. In the present embodiment, again, the geometric shape R2 is a rectangle. However, the form of the geometric shape R2 is not limited to a rectangle. The size of the geometric shape R2 in the depth direction varies with the frequency of the first ultrasound.

Figure 26:
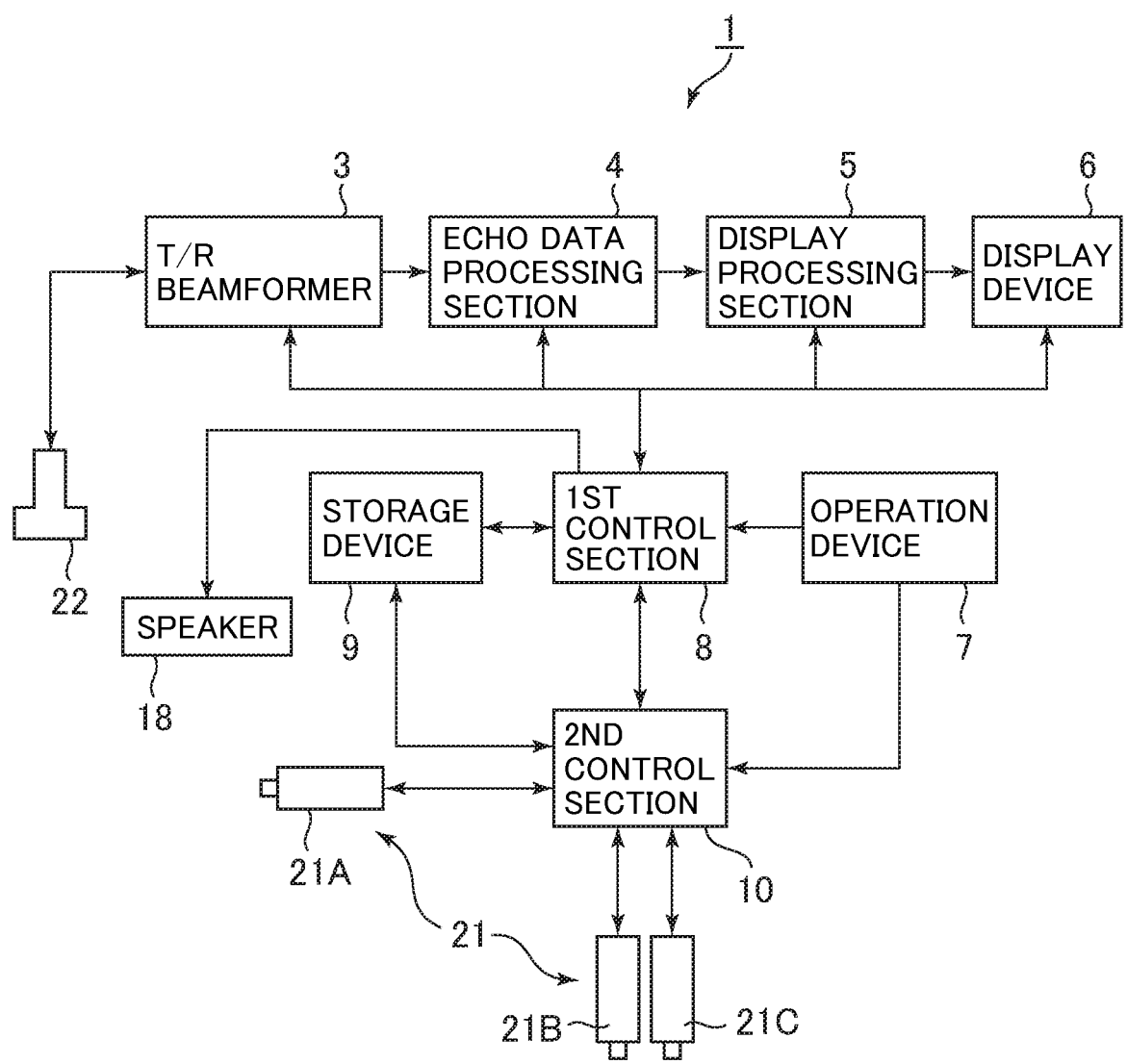
FIG. 26 is a block diagram showing a configuration of the ultrasonic diagnostic apparatus comprising a speaker.

Furthermore, instead of or along with displaying the first ultrasonic probe 21 by characters or a geometric shape or displaying the frequency of the first ultrasound, the first ultrasonic probe 21 or the frequency may be audibly notified by a speaker 18 shown in FIG. 26. In this case, the speaker 18 is an exemplary embodiment of the notifying section in the present invention.

While a case in which the speaker 18 is provided in the ultrasonic diagnostic apparatus 1 shown in FIG. 1 is illustrated in FIG. 26, it will be easily recognized that the speaker may be provided in any one of the apparatuses described earlier in the other embodiments.

In addition, the first control section 8, and second control sections 10, 151 may be constructed as a single control section.

We claim:

1. An ultrasonic diagnostic system comprising:
   a vibrator for applying mechanical vibration to a subject to generate shear waves in said subject;
   at least one first transceiver for performing transmission/reception of first ultrasound for detecting said shear waves generated in said subject by said mechanical vibration applied by said vibrator;
   a second transceiver for performing transmission/reception of second ultrasound different from said first ultrasound to/from said subject; and
   a processor configured to:
   drive said second transceiver to transmit said second ultrasound;
   calculate a value of a parameter affecting a most suitable frequency of the first ultrasound to be transmitted from said first transceiver based on echo signals obtained by transmission/reception of said second ultrasound, wherein the value of said parameter is at least one of an amount of ultrasound attenuation in said subject, and a distance from a body surface to a diaphragm of said subject;
   identify the most suitable frequency of the first ultrasound based on the value of the parameter;
   control said vibrator to apply the mechanical vibration to said subject and
   drive said first transceiver to transmit said first ultrasound at the most suitable frequency to detect the shear waves after said mechanical vibration is applied.

2. The ultrasonic diagnostic system as recited in claim 1, wherein: said system comprises an ultrasonic diagnostic apparatus connected with said vibrator, said first transceiver, and said second transceiver.

3. The ultrasonic diagnostic system as recited in claim 1, comprising:
   a first apparatus connected with said vibrator and said first transceiver; and
   a second apparatus connected with said second transceiver.

4. The ultrasonic diagnostic system as recited in claim 1, comprising:
   a first apparatus connected with said vibrator;
   a second apparatus connected with said first transceiver and said second transceiver.

5. The ultrasonic diagnostic system as recited in claim 1, comprising:
   a first apparatus connected with said vibrator;
   a second apparatus connected with said first transceiver; and
   a third apparatus connected with said second transceiver.

6. The ultrasonic diagnostic system as recited in claim 1, wherein the processor is further configured to:
create data for an ultrasonic image of said subject based on the echo signals obtained by transmission/reception of said second ultrasound, wherein
the value of said parameter is based on the data for said ultrasonic image.

7. The ultrasonic diagnostic system as recited in claim 1, wherein:
the value of said parameter is an amount of attenuation of said first ultrasound; and
said processor calculates the amount of attenuation of said first ultrasound based on the echo signal obtained by transmission/reception of said second ultrasound for one acoustic line.

8. The ultrasonic diagnostic system as recited in claim 1, wherein: said vibrator and said first transceiver are configured as a single unit or separate units.

9. The ultrasonic diagnostic system as recited in claim 1, wherein said processor is further configured to calculate a velocity of propagation of said shear waves based on echo signals from said first ultrasound.

10. The ultrasonic diagnostic system as recited in claim 1, wherein:
said at least one first transceiver comprises a plurality of first transceivers, wherein each of the plurality of first transceivers is configured to emit the first ultrasound at a different frequency and
said processor is further configured to identify one of the plurality of first transceivers based on the most suitable frequency, wherein the processor is configured to drive the first transceiver to transmit the first ultrasound at the most suitable frequency by driving the one of the plurality of first transceivers at the most suitable frequency.

11. The ultrasonic diagnostic system as recited in claim 10, further comprising an operation device,
wherein said processor is further configured to notify an operator of said most suitable frequency or said identified one of the plurality of first transceivers having the most suitable frequency,
wherein said operation device accepts an input to identify the one of the plurality of first transceivers that is configured to transmit/receive the first ultrasound at the most suitable frequency,
wherein said first ultrasound is transmitted from the one of the plurality of first transceivers based on said input.

12. The ultrasonic diagnostic system as recited in claim 1, wherein:
said at least one first transceiver is comprised of one first transceiver capable of transmitting a plurality of kinds of first ultrasound each having a different frequency, and
said processor identifies one of the plurality of kinds of first ultrasound based on the most suitable frequency determined based on the value of the parameter.

13. An ultrasonic diagnostic system comprising:
a vibrator for applying mechanical vibration to a subject to generate shear waves in said subject;
a transceiver for performing transmission/reception of first ultrasound for detecting said shear waves generated in said subject by said mechanical vibration applied by said vibrator and transmission/reception of second ultrasound different from said first ultrasound to/from said subject; and
a processor configured to:
calculate a value of a parameter affecting a most suitable frequency of the first ultrasound to be transmitted from said transceiver based on echo signals obtained by transmission/reception of said second ultrasound, wherein the value of said parameter is at least one of an amount of ultrasound attenuation in said subject, and a distance from a body surface to a diaphragm of said subject;
identify the most suitable frequency of the first ultrasound to be transmitted/received at the transceiver based on the value of said parameter;
control said vibrator to apply the mechanical vibration to said subject and
drive said transceiver to transmit said first ultrasound at the most suitable frequency after said mechanical vibration is applied.

14. The ultrasonic diagnostic system as recited in claim 13, wherein: said system comprises an ultrasonic diagnostic apparatus connected with said vibrator and said transceiver.

15. The ultrasonic diagnostic system as recited in claim 13, comprising:
a first apparatus connected with said vibrator; and
a second apparatus connected with said transceiver.

16. The ultrasonic diagnostic system as recited in claim 13, wherein: said vibrator and said transceiver are configured as a single unit or separate units.

* * * * *